US010017784B2

(12) United States Patent
Mitomo et al.

(10) Patent No.: US 10,017,784 B2
(45) Date of Patent: Jul. 10, 2018

(54) GENE TRANSFER INTO AIRWAY EPITHELIAL STEM CELL BY USING LENTIVIRAL VECTOR PSEUDOTYPED WITH RNA VIRUS OR DNA VIRUS SPIKE PROTEIN

(71) Applicant: DNAVEC Corporation, Ibaraki (JP)

(72) Inventors: Katsuyuki Mitomo, Ibaraki (JP); Makoto Inoue, Ibaraki (JP); Hitoshi Iwasaki, Ibaraki (JP); Mamoru Hasegawa, Ibaraki (JP); Eric W. Alton, London (GB); Uta Griesenbach, London (GB)

(73) Assignee: ID PHARMA CO., LTD., Tsukuba (JP)

( * ) Notice: Subject to any disclaimer, the term of this patent is extended or adjusted under 35 U.S.C. 154(b) by 0 days.

(21) Appl. No.: 14/543,689

(22) Filed: Nov. 17, 2014

(65) Prior Publication Data

US 2015/0174198 A1 Jun. 25, 2015

Related U.S. Application Data

(63) Continuation of application No. 12/091,646, filed as application No. PCT/JP2006/321517 on Oct. 27, 2006.

(30) Foreign Application Priority Data

Oct. 28, 2005 (JP) ................................ 2005-313971

(51) Int. Cl.

| | |
|---|---|
| ***A61K 48/00*** | (2006.01) |
| ***C12N 15/867*** | (2006.01) |
| ***C12N 15/10*** | (2006.01) |
| ***A61K 39/21*** | (2006.01) |
| ***C12N 15/11*** | (2006.01) |
| ***C12N 15/45*** | (2006.01) |
| ***C12N 15/86*** | (2006.01) |
| ***A61K 38/17*** | (2006.01) |
| ***C07K 14/47*** | (2006.01) |
| ***C12N 5/071*** | (2010.01) |
| ***A61K 9/00*** | (2006.01) |
| ***A61K 38/16*** | (2006.01) |
| ***C12N 7/00*** | (2006.01) |

(52) U.S. Cl.

CPC ............ *C12N 15/86* (2013.01); *A61K 9/0043* (2013.01); *A61K 38/162* (2013.01); *A61K 38/177* (2013.01); *A61K 38/1709* (2013.01); *C07K 14/4712* (2013.01); *C12N 5/0688* (2013.01); *C12N 7/00* (2013.01); *A61K 48/00* (2013.01); *C12N 2510/00* (2013.01); *C12N 2740/15033* (2013.01); *C12N 2740/15043* (2013.01); *C12N 2740/15045* (2013.01); *C12N 2810/609* (2013.01); *C12N 2810/6072* (2013.01)

(58) Field of Classification Search

None

See application file for complete search history.

(56) References Cited

U.S. PATENT DOCUMENTS

| | | | |
|---|---|---|---|
| 5,162,215 | A | 11/1992 | Bosselman et al. |
| 5,576,201 | A | 11/1996 | Mason et al. |
| 5,962,274 | A | 10/1999 | Parks |
| 6,040,174 | A | 3/2000 | Imler et al. |
| 6,323,031 | B1 | 11/2001 | Cichutek |
| 6,645,760 | B2 | 11/2003 | Nagai et al. |
| 6,723,532 | B2 | 4/2004 | Nagai et al. |
| 6,743,620 | B1 | 6/2004 | Iba et al. |
| 6,746,860 | B1 | 6/2004 | Tokusumi et al. |
| 6,749,863 | B1 | 6/2004 | Chang et al. |
| 6,828,138 | B1 | 12/2004 | Nagai et al. |
| 7,101,685 | B2 | 9/2006 | Nagai et al. |
| 7,144,579 | B2 | 12/2006 | Nagai et al. |
| 7,226,786 | B2 | 6/2007 | Kitazato et al. |
| 7,314,614 | B1 | 1/2008 | Yonemitsu et al. |
| 7,323,337 | B2 | 1/2008 | Hanazono et al. |
| 7,510,706 | B2 | 3/2009 | Yonemitsu et al. |
| 2002/0002143 | A1 | 1/2002 | Kano et al. |
| 2002/0169306 | A1 | 11/2002 | Kitazato et al. |
| 2003/0166252 | A1 | 9/2003 | Kitazato et al. |
| 2003/0170210 | A1 | 9/2003 | Masaki et al. |

(Continued)

FOREIGN PATENT DOCUMENTS

| | | | |
|---|---|---|---|
| EP | 0 863 202 | A1 | 9/1998 |
| EP | 0 864 645 | A1 | 9/1998 |

(Continued)

OTHER PUBLICATIONS

Gill et al, The development of gene therapy for diseases of the lung, Cell. Mol. Life Sci. 61 (2004) 355-368.*

Patent Examination Policy—MPEP Staff—35 USC 112 1st para—Enablement of Chemical/Biotechnical Applications, http://www.uspto.gov/patent/laws-and-regulations/patent-examination-policy-mpep-staff- . . . Nov. 11, 2015, pp. 1-68.*

Agrawal et al., "Cell-Cycle Kinetics and VSV-G Pseudotyped Retrovirus-Mediated Gene Transfer in Blood-Derived $CD34^+$ Cells," *Exp. Hematol.* 24(6):738-747 (1996).

Ali and Nayak, "Assembly of Sendai Virus: M Protein Interacts with F and HN Proteins and with the Cytoplasmic Tail and Transmembrane Domain of F Protein," *Virology* 276(2):289-303 (2000).

Altenschmidt et al., "Specific Cytotoxic T Lymphocytes in Gene Therapy," *J. Mol. Med.* 75(4):259-266 (1997).

Amit et al., "Clonally Derived Human Embryonic Stem Cell Lines Maintain Pluripotency and Proliferative Potential For Prolonged Periods of Culture," *Dev. Biol.* 227(2):271-278 (2000).

(Continued)

*Primary Examiner* — Maria Marvich

(74) *Attorney, Agent, or Firm* — Seed IP Law Group LLP

(57) ABSTRACT

The present inventors successfully introduced genes into stem cells of airway epithelial tissues using simian immunodeficiency virus vectors pseudotyped with F and HN, which are envelope glycoproteins of Sendai virus. Gene transfer into airway epithelial tissue stem cells using a vector of the present invention is useful for gene therapy of genetic respiratory diseases such as cystic fibrosis. Furthermore, it is possible to select respiratory organs such as the lungs as production tissues for providing proteins that are deficient due to genetic diseases.

8 Claims, 8 Drawing Sheets

(56) References Cited

U.S. PATENT DOCUMENTS

| | | | | |
|---|---|---|---|---|
| 2003/0170897 | A1 | 9/2003 | Imai et al. | |
| 2003/0203489 | A1 | 10/2003 | Yonemitsu et al. | |
| 2004/0005296 | A1 | 1/2004 | Yonemitsu et al. | |
| 2004/0053877 | A1 | 3/2004 | Fukumura et al. | |
| 2004/0101965 | A1 | 5/2004 | Griesenbach et al. | |
| 2005/0100890 | A1 | 5/2005 | Davidson et al. | 12/5 |
| 2005/0113298 | A1 | 5/2005 | Farzan et al. | |
| 2005/0250718 | A1 | 11/2005 | Sakakibara et al. | |
| 2005/0255123 | A1 | 11/2005 | Wilson et al. | |
| 2006/0128019 | A1 | 6/2006 | Kobayashi et al. | |
| 2007/0009949 | A1 | 1/2007 | Kitazato et al. | |

FOREIGN PATENT DOCUMENTS

| | | | |
|---|---|---|---|
| EP | 1 179 594 | A1 | 2/2002 |
| JP | 7-509616 | A1 | 10/1995 |
| JP | 10-506542 | A1 | 6/1998 |
| JP | 2002-159289 | A | 6/2002 |
| WO | 97/16171 | | 5/1997 |
| WO | 97/16538 | | 5/1997 |
| WO | 98/27217 | | 6/1998 |
| WO | 99/13905 | | 3/1999 |
| WO | 00/27430 | | 5/2000 |
| WO | 00/70055 | | 11/2000 |
| WO | 00/70070 | | 11/2000 |
| WO | 01/32898 | | 5/2001 |
| WO | 01/92508 | | 12/2001 |
| WO | 02/38726 | | 5/2002 |
| WO | 02/101057 | | 12/2002 |
| WO | 03/066868 | | 8/2003 |
| WO | 03/092738 | | 11/2003 |
| WO | 03/093476 | | 11/2003 |
| WO | 03/102183 | | 12/2003 |
| WO | 2004/022731 | | 3/2004 |
| WO | 2004/038029 | | 5/2004 |
| WO | 2005/087936 | | 9/2005 |

OTHER PUBLICATIONS

Anderson, "Human Gene Therapy," *Nature* 392(6679 Suppl.):25-30 (1998).

Asano et al., "Highly Efficient Gene Transfer into Primate Embryonic Stem Cells with a Simian Lentivirus Vector," *Mol. Ther.* 6(2):162-168 (2002).

Auricchio et al., "Noninvasive Gene Transfer to the Lung for Systemic Delivery of Therapeutic Proteins," *J. Clin. Invest.* 110(4):499-504 (2002).

Auten et al., "Effect of Scaffold Attachment Region on Transgene Expression in Retrovirus Vector-Transduced Primary T Cells and Macrophages," *Hum. Gene Ther.* 10(8):1389-1399 (1999).

Avril-Delplanque et al., "Aquaporin-3 Expression in Human Fetal Airway Epithelial Progenitor Cells," *Stem Cells* 23(7):992-1001 (2005).

Ayuk et al., "Establishment of an Optimised Gene Transfer Protocol for Human Primary T Lymphocytes According to Clinical Requirements," *Gene Ther.* 6(10):1788-1792 (1999).

Bagai et al., "Hemagglutinin-Neuraminidase Enhances F Protein-Mediated Membrane Fusion of Reconstituted Sendai Virus Envelopes with Cells," *J. Virol.* 67(6):3312-3318 (1993).

Baker et al., "Polyethylenimine (PEI) is a Simple, Inexpensive and Effective Reagent for Condensing and Linking Plasmid DNA to Adenovirus for Gene Delivery," *Gene Ther.* 4(8):773-782 (1997).

Barclay and Palese, "Influenza B Viruses with Site-Specific Mutations Introduced into the HA Gene," *J. Virol.* 69(2):1275-1279 (1995).

Bitzer et al., "Sendai Virus Efficiently Infects Cells Via the Asialoglycoprotein Receptor and Requires the Presence of Cleaved $F_o$ Precursor Proteins for this Alternative Route of Cell Entry," J. Virol. 71 (7):5481-5486 (1997).

Blaese et al., "T Lymphocyte-Directed Gene Therapy for ADA—SCID: Initial Trial Results After 4 Years," *Science* 270(5235):475-480 (1995).

Borthwick et al., "Evidence for Stem-Cell Niches in the Tracheal Epithelium," *Am. J. Respir. Cell Mol. Biol.* 24(6):662-670 (2001).

Bosch et al., "Inhibition of Release of Lentivirus Particles with Incorporated Human Influenza Virus Haemagglutinin by Binding to Sialic Acid-Containing Cellular Receptors," *J. Gen. Virol.* 82(Pt. 10):2485-2494 (2001).

Brenner, "Gene Transfer to Hematopoietic Cells," *N. Engl. J. Med.* 335(5):337-339 (1996).

Brown and Rose, "Sorting of GPI-Anchored Proteins to Glycolipid-Enriched Membrane Subdomains during Transport to the Apical Cell Surface," *Cell* 68(3):533-544 (1992).

Buchschacher and Wong-Staal, "Development of Lentiviral Vectors for Gene Therapy for Human Diseases," *Blood* 95(8):2499-2504 (2000).

Bunnell et al., "Efficient In Vivo Marking of Primary $CD4^+$ T Lymphocytes in Nonhuman Primates Using a Gibbon Ape Leukemia Virus-Derived Retroviral Vector," *Blood* 89(6):1987-1995 (1997).

Burns et al., "Vesicular Stomatitis Virus G Glycoprotein Pseudotyped Retroviral Vectors: Concentration to Very High Titer and Efficient Gene Transfer into Mammalian and Nonmammalian Cells," *Proc. Natl. Acad. Sci. USA* 90(17):8033-8037 (1993).

Carpenter et al., "Generation of Neurons and Hepatocyte-Like Cells from Human Embryonic Stem Cells," *Pluripotent Stem Cells: Biology and Applications, Keystone Symposium* Abstract 46 (Feb. 6-11, 2001).

Carpenter et al., Summary of Numerical Data Presented in a Slide Presentation Entitled "Generation of Neurons and Hepatocyte-Like Cells from Human Embryonic Stem Cells," at the *Pluripotent Stem Cells: Biology and Applications, Keystone Symposium* (Feb. 2001).

Cathomen et al., "A Matrix-Less Measles Virus Is Infectious and Elicits Extensive Cell Fusion: Consequences for Propagation in the Brain," *EMBO J.* 17(14):3899-3908 (1998).

Check, "Cancer Risk Prompts US to Curb Gene Therapy," *Nature* 422(6927):7 (2003).

Cherry et al., "Retroviral Expression in Embryonic Stem Cells and Hematopoietic Stem Cells," *Mol. Cell Biol.* 20:7419-7426 (2000).

Cicala et al., "HIV Envelope Induces a Cascade of Cell Signals in Non-Proliferating Target Cells that Favor Virus Replication," *Proc. Natl. Acad. Sci. USA* 99:9380-9385 (2002).

Compans et al., "Effect of Antibody to Neuraminidase on the Maturation and Hemagglutinating Activity of an Influenza $A_2$ Virus," *J. Virol.* 4(4):528-534 (1969).

Conley et al., "Derivation, Propagation and Differentiation of Human Embryonic Stem Cells," *Int. J. Biochem. Cell Biol.* 36(4):555-567 (2004).

Conzelmann, "Nonsegmented Negative-Strand RNA Viruses: Genetics and Manipulation of Viral Genomes," *Annu. Rev. Genet.* 32:123-162 (1998).

Copreni et al., Lentivirus-Mediated Gene Transfer to the Respiratory Epithelium: A Promising Approach to Gene Therapy of Cystic Fibrosis: *Gene Ther.* 11 :S67-S75, 2004.

Costello et al., "Gene Transfer into Stimulated and Unstimulated T Lymphocytes by HIV-1-Derived Lentiviral Vectors," *Gene Ther.* 7(7):596-604 (2000).

Couzin et al., "Gene Therapy. As Gelsinger Case Ends, Gene Therapy Suffers Another Blow," *Science* 307(5712):1028 (2005).

Crennell et al., "Crystal Structure of the Multifunctional Paramyxovirus Hemagglutinin-Neuraminidase," *Nat. Struct. Bioi.* 7(11): 1068-1074 (2000).

Dardalhon et al., "Lentivirus-mediated Gene Transfer in Primary T Cells Is Enhanced by a Central DNA Flap," *Gene Ther.* 8(3):190-198 (2001).

Di Nicola et al., "Recombinant Adenoviral Vector-LipofectAMINE Complex for Gene Transduction into Human T Lymphocytes," *Hum. Gene Ther.* 10(11):1875-1884 (1999).

Dong et al., "A Chimeric Avian Retrovirus Containing the Influenza Virus Hemagglutinin Gene Has an Expanded Host Range," *J. Virol.* 66(12):7374-7382 (1992).

Donovan and de Miguel, "Pluripotent Embryonic Germ Cell Lines," *Pluripotent Stem Cells: Biology and Applications, Keystone Symposium* Abstract 34 (Feb. 6-11, 2001).

(56) References Cited

OTHER PUBLICATIONS

Donovan, "Pluripotent Stem Cells," *IMSUT Symposium for Stem Cell Biology Proceedings* Abstract 67 (Jun. 22-24, 2000).
Donovan, Summary of Numerical Data Presented in a Slide Presentation Entitled "Pluripotent Embryonic Germ Cell Lines," at the *Pluripotent Stem Cells: Biology and Applications, Keystone Symposium* (Feb. 2001).
Donovan, Summary of Numerical Data Presented in a Slide Presentation Entitled "Pluripotent Stem Cells," at the *IMSUT Symposium for Stem Cell Biology Proceedings* (Jun. 2000).
Douglas et al., "Targeted Gene Delivery by Tropism-Modified Adenoviral Vectors," *Nat. Biotechnol.* 14(11):1574-1578 (1996).
Duan et al., "Lef1 Transcription Factor Expression Defines Airway Progenitor Cell Targets for In Utero Gene Therapy of Submucosal Gland in Cystic Fibrosis," *Am. J. Respir. Cell Mol. Biol.* 18(6):750-758 (1998).
Eiges et al., "Establishment of Human Embryonic Stem Cell-Transfected Clones Carrying a Marker for Undifferentiated Cells," *Curr. Biol.* 11 (7):514-518 (2001).
Engelhardt, "Stem Cell Niches in the Mouse Airway," *Am. J. Respir. Cell. Mol. Biol.* 24(6):649-652 (2001).
Engelhardt, "The Lung as a Metabolic Factory for Gene Therapy," *J. Clin. Invest.* 110(4):429-432 (2002).
Flint et al., "Characterization of Hepatitis C Virus E2 Glycoprotein Interaction with a Putative Cellular Receptor, CD81," *J. Virol.* 73:6235-6244 (1999).
Friedman, "Expression of Human Adenosine Deaminase Using a Transmissable Murine Retrovirus Vector System," *Proc. Natl. Acad. Sci. USA* 82(3):703-707 (1985).
Gardlik et al., "Vectors and Delivery Systems in Gene Therapy," *Med. Sci. Monit.* 11 (4):RA110-RA121 (2005).
Garoff et al., "Virus Maturation by Budding," *Microbiol. Mol. Biol. Rev.* 62(4):1171-1190 (1998).
Giangreco et al., "Molecular Phenotype of Airway Side Population Cells," *Am. J. Physiol. Lung Cell Mol. Physiol.* 286(4):L624-L630 (2004). E-published on Aug. 8, 2003.
Gitman et al., "Use of Virus-Attached Antibodies or Insulin Molecules to Mediate Fusion Between Sendai Virus Envelopes and Neuraminidase-Treated Cells," *Biochemistry* 24(11):2762-2768.
Gladow et al., "MLV-10A1 Retrovirus Pseudotype Efficiently Transduces Primary Human $CD4^+$ T Lymphocytes," *J. Gene Med.* 2(6):409-415 (2000).
Gonçalves, "A Concise Peer into the Background, Initial Thoughts and Practices of Human Gene Therapy," *BioEssays* 27(5):506-517 (2005).
Griffin et al., "Effects of Hexose Starvation and the Role of Sialic Acid in Influenza Virus Release," *Virology* 125(2):324-334 (1983).
Gropp et al., "Stable Genetic Modification of Human Embryonic Stem Cells by Lentiviral Vectors," *Mol. Ther.* 7(2): 281-287 (2003).
Hamaguchi et al., "Lentivirus Vector Gene Expression during ES Cell-Derived Hematopoietic Development In Vitro," *J. Virol.* 74(22):10778-10784 (2000).
Hanazono et al., "Genetic Manipulation of Primate Embryonic and Hematopoietic Stem Cells with Simian Lentivirus Vectors," *Trends Cardiovasc. Med.* 13(3):106-110 (2003).
Hanazono et al., "Highly Efficient Gene Transfer into Cynomolgus Monkey Embryonic Stem Cells with a Simian Lentivirus Vector," *Blood* 98(11 part 1):746a (2001) (Abstract No. 3106).
Hasan et al., "Creation of an Infectious Recombinant Sendai Virus Expressing the Firefly Luciferase Gene from the 3' Proximal First Locus," *J. Gen. Virol.* 78(Pt 11):2813-2820 (1997).
Hatziioannou et al., "Incorporation of Fowl Plague Virus Hemagglutinin into Murine Leukemia Virus Particles and Analysis of the Infectivity of the Pseudotyped Retroviruses," *J. Virol.* 72(6):5313-5317 (1998).
Hege and Roberts, "T-Cell Gene Therapy," *Curr. Opin. Biotechnol.* 7(6):629-634 (1996).
Heggeness et al., "In Vitro Assembly of the Nonglycosylated Membrane Protein (M) of Sendai Virus," *Proc. Natl. Acad. Sci. USA* 79(20):6232-6236 (1982).
Hong et al., "Basal Cells Are a Multipotent Progenitor Capable of Renewing the Bronchial Epithelium," *Am. J. Pathol.* 164(2):577-588 (2004).
Hong et al., "In Vivo Differentiation Potential of Tracheal Basal Cells: Evidence for Multipotent and Unipotent Subpopulations," *Am. J. Physiol. Lung Cell Physiol.* 286(4):L643-L649 (2004). E-published on Jul. 18, 2003.
Huntley et al., "Phosphorylation of Sendai Virus Phosphoprotein by Cellular Protein Kinase C ζ," *J. Bioi. Chem.*272(26):16578-16584 (1997).
Ikeda et al., "Recombinant Sendai Virus-Mediated Gene Transfer into Adult Rat Retinal Tissue: Efficient Gene Transfer by Brief Exposure," *Exp. Eye Res.* 75(1):39-48 (2002).
Imbert et al., "Highly Efficient Retroviral Gene Transfer into Human Primary T Lymphocytes Derived from Peripheral Blood," *Cancer Gene Ther.* 1(4):259-265 (1994).
Inoue et al., "A New Sendai Virus Vector Deficient in the Matrix Gene Does Not Form Virus Particles and Shows Extensive Cell-to-Cell Spreading," *J. Virol.* 77(11):6419-6429 (2003).
Juengst, "What Next for Human Gene Therapy? Gene Transfer Often has Multiple and Unpredictable Effects on Cells," *BMJ* 326(7404):1410-1411 (2003).
Jung et al., "Lentiviruses Inefficiently Incorporate Human Parainfluenza Type 3 Envelope Proteins," *Biotechnol. Bioeng.* 99(4): 1016-1027 (2008).
Kahl et al., "Lentiviral Vectors Pseudotyped with Glycoproteins from Ross River and Vesicular Stomatitis Viruses: Variable Transduction Related to Cell Type and Culture Conditions," *Mol. Ther.* 11 :470-482 (2005).
Karron et al., "Respiratory Syncytial Virus (RSV) SH and G Proteins Are Not Essential for Viral Replication In Vitro: Clinical Evaluation and Molecular Characterization of a Cold-Passaged, Attenuated RSV Subgroup B Mutant," *Proc. Natl. Acad. Sci. USA* 94:13961-13966 (1997).
Kato et al., "Initiation of Sendai Virus Multiplication from Transfected cDNA or RNA with Negative or Positive Sense," *Genes to Cells* 1(6):569-579 (1996).
Kido et al., "The Human Mucus Protease Inhibitor and its Mutants Are Novel Defensive Compounds Against Infection with Influenza A and Sendai Viruses," *Biopolymers* (*Peptide Science*) 51 :79-86 (1999).
Klink et al., "Gene Delivery Systems—Gene Therapy Vectors for Cystic Fibrosis," *J. Cyst. Fibros.* 3:203-212, 2004.
Kobayashi et al., "Pseudotyped Lentivirus Vectors Derived from Simian Immunodeficiency Virus SIVagm with Envelope Glycoproteins from Paramyxovirus," *J. Virol.* 77(4):2607-2614 (2003).
Kobinger et al., "Filovirus-Pseudotyped Lentiviral Vector Can Efficiently and Stably Transduce Airway Epithelia In Vivo," *Nat. Biotechnol.* 19(3):225-230 (2001).
Koehler et al., "Protection of Cftr Knockout Mice from Acute Lung Infection by a Helper-Dependent Adenoviral Vector Expressing Cftr in Airway Epithelia," *Proc. Natl. Acad. Sci. USA* 100(26):15364-15369 (2003). E-published on Dec. 12, 2003.
Kondo et al., "Temperature-Sensitive Phenotype of a Mutant Sendai Virus Strain Is Caused by Its Insufficient Accumulation of the M Protein," *J. Biol. Chem.* 268(29):21924-21930 (1993).
Kühlcke et al., "Highly Efficient Retroviral Gene Transfer Based on Centrifugation-Mediated Vector Preloading of Tissue Culture Vessels," *Mol. Ther.* 5(4):473-478 (2002).
Kumar et al., "Systematic Determination of the Packaging Limit of Lentiviral Vectors," *Hum. Gene Ther.* 12(15):1893-1905 (2001). (Abstract only).
Lamb and Kolakofsky, "Paramyxoviridae: The Viruses and Their Replication," *Fields Virology*, 3rd ed., B.N. Fields et al., Lippincott-Raven Publishers, Philadelphia, Chapter 40, p. 1177-1178 (1996).
Langedijk et al., "Sequence and Structure Alignment of Paramyxoviridae Attachment Proteins and Discovery of Enzymatic Activity for a Morbillivirus Hemagglutinin," *J. Virol.* 71 (8):6155-6167 (1997).

(56) References Cited

OTHER PUBLICATIONS

Leyrer et al., "Sendai Virus-Like Particles Devoid of Haemagglutinin-Neuraminidase Protein Infect Cells Via the Human Asialoglycoprotein Receptor," *J. Gen. Virol.* 79(Pt. 4):683-687 (1998).
Li et al., "A Cytoplasmic RNA Vector Derived from Nontransmissible Sendai Virus with Efficient Gene Transfer and Expression," *J. Virol.* 74(14):6564-6569 (2000).
Limberis et al., "Recovery of Airway Cystic Fibrosis Transmembrane Conductance Regulator Function in Mice with Cystic Fibrosis after Single-Dose Lentivirus-Mediated Gene Transfer," *Hum. Gene Ther.* 13(16):1961-1970 (2002).
Lin and Cannon, "Use of Pseudotyped Retroviral Vectors to Analyze the Receptor-Binding Pocket of Hemagglutinin from a Pathogenic Avian Influenza A Virus (H7 Subtype)," *Virus Res.* 83(1-2):43-56 (2002).
Lin et al., "The RNA Binding Region of the Paramyxovirus SV5 V and P Proteins," *Virology* 238(2):460-469 (1997).
Liu et al., "Influenza Type A Virus Neuraminidase Does Not Play a Role in Viral Entry, Replication, Assembly, or Budding," *J. Virol.* 69(2):1099-1106 (1995).
Liu et al., "Pseudotransduction of Hepatocytes by Using Concentrated Pseudotyped Vesicular Stomatitis Virus G Glycoprotein (VSV-G)—Moloney Murine Leukemia Virus-Derived Retrovirus Vectors: Comparison of VSV-G and Amphotropic Vectors for Hepatic Gene Transfer," *J. Virol.* 70(4):2497-2502 (1996).
Ma et al., "High-Level Sustained Transgene Expression in Human Embryonic Stem Cells Using Lentiviral Vectors," *Stem Cells* 21 (1):111-117 (2003).
Mangeot et al., "Development of Minimal Lentivirus Vectors Derived from Simian Immunodeficiency Virus (SIVmac251) and Their Use for Gene Transfer into Human Dendritic Cells," *J. Virol.* 74(18):8307-8315 (2000).
Manie et al., "Measles Virus Structural Components Are Enriched into Lipid Raft Microdomains: A Potential Cellular Location for Virus Assembly," *J. Virol.* 74(1):305-311 (2000).
Markwell et al., "An Alternative Route of Infection for Viruses: Entry by Means of the Asialoglycoprotein Receptor of a Sendai Virus Mutant Lacking its Attachment Protein," *Proc. Natl. Acad. Sci. USA* 82(4):978-982 (1985).
Matsumura et al., "RNA Editing-Like Phenomenon in Paramyxovirus V Gene mRNA Observed in Insect Cells Infected With a Recombinant Baculovirus," *J. Gen. Virol.* 80(Pt. 1):117-123 (1999).
McKay et al., "Influenza M2 Envelope Protein Augments Avian Influenza Hemagglutinin Pseudotyping of Lentiviral Vectors," *Gene Ther.* 13(8):715-724 (2006).
Mebatsion et al., "Matrix Protein of Rabies Virus Is Responsible for the Assembly and Budding of Bullet-Shaped Particles and Interacts with the Transmembrane Spike Glycoprotein G," *J. Virol.* 73(1):242-250 (1999).
Misaki et al., "Gene-Transferred Oligoclonal T Cells Predominantly Persist in Peripheral Blood from an Adenosine Deaminase-Deficient Patient During Gene Therapy," *Mol. Ther.* 3(1):24-27 (2001).
Mitomo et al., "A Gene Is Successfully Transferred into Airway Tissues by Using a Monkey Immunodeficiency Virus Vector Having Been Pseudotyped with Sendai Virus Envelope Glycoproteins F and HN," The Japanese Society for Virology Gakujutsu Shukai Sokai Program Shorokushu vol. 52, p. 377 (Abstract #3E16) (2004). English language translation.
Mitomo et al., "Towards Cystic Fibrosis and Airway Gene Therapy: Evaluation of EGFP Gene Expression in Murine Nasal Airways Mediated by Simian Immunodeficiency Virus Vectors Pseudotyped with Sendai Virus Glycoproteins F and HN," *Molecular Therapy* 11(Supplement 1):S139, 2005; Abstract 355.
Miura et al., "HVJ (Sendai Virus)-Induced Envelope Fusion and Cell Fusion Are Blocked by Monoclonal Anti-HN Protein Antibody That Does Not Inhibit Hemagglutination Activity of HVJ," *Exp. Cell Res.* 141 (2):409-420 (1982).
Moore and Lemischka, "Stem Cells and Their Niches," *Science* 311 (5769):1880-1885 (2006).
Morikawa et al., "Characterization of Temperature-Sensitive Mutants of Measles Virus," *Kitasato Arch. of Exp. Med.* 64(1):15-30 (1991).
Morrison et al., "Complementation between Avirulent Newcastle Disease Virus and a Fusion Protein Gene Expressed from a Retrovirus Vector: Requirements for Membrane Fusion," *J. Virol.* 65(2):813-822 (1991).
Morse et al., "Optimizing Influenza Hemagglutinin Pseudotyping of Equine Lentiviral Vectors," *Mol. Ther.* 5 (Pt. 2):S38 (abstract 110) (2002).
Movassagh et al., "Retrovirus-Mediated Gene Transfer into T Cells: 95% Transduction Efficiency Without Further In Vitro Selection," *Hum. Gene Ther.* 11 (8):1189-1200 (2000).
Nagai, "Paramyxovirus Replication and Pathogenesis. Reverse Genetics Transforms Understanding," *Rev. Med. Virol.* 9(2):83-99 (1999).
Nagata et al., "Efficient Gene Transfer of a Simian Immunodeficiency Viral Vector into Cardiomyocytes Derived from Primate Embryonic Stem Cells," *J. Gene Med.* 5(11):921-928, (2003).
Nakajima et al., "Development of Novel Simian Immunodeficiency Virus Vectors Carrying a Dual Gene Expression System," *Hum. Gene Ther.* 11(13):1863-1874 (2000).
Négre et al., "Characterization of Novel Safe Lentiviral Vectors Derived from Simian Immunodeficiency Virus (SIVmac251) that Efficiently Transduce Mature Human Dendritic Cells," *Gene Ther.* 7(19):1613-1623 (2000).
Neil et al., "Postentry Restriction to Human Immunodeficiency Virus-Based Vector Transduction in Human Monocytes," *J. Virol.* 75:5448-5456 (2001).
Odorico et al., "Multilineage Differentiation from Human Embryonic Stem Cell Lines," *Stem Cells* 19(3):193-204 (2001).
Okano et al., "Recombinant Sendai Virus Vectors for Activated T Lymphocytes," *Gene Ther.* 10(16):1381-1391 (2003).
Palese et al., "Characterization of Temperature Sensitive Influenza Virus Mutants Defective in Neuraminidase," *Virology* 61 (2):397-410 (1974).
Parks and Lamb, "Role of NH2-terminal Positively Charged Residues in Establishing Membrane Protein Topology," *J. Biol. Chem.* 268(25):19101-19109 (1993).
Paterson et al., "Expression at the Cell Surface of Biologically Active Fusion and Hemagglutinin/Neuraminidase Proteins of the Paramyxovirus Simian Virus 5 from Cloned cDNA," *Proc. Nat. Acad. Sci. USA* 82(22):7520-7524 (1985).
Pera et al., "Human Embryonic Stem Cells," *J. Cell. Sci.* 113(Pt. 1):5-10 (2000).
Pfeifer et al., "Transgenesis by Lentiviral Vectors: Lack of Gene Silencing in Mammalian Embryonic Stem Cells and Preimplantation Embryos," *Proc. Natl. Acad. Sci. USA* 99(4):2140-2145 (2002).
Pollok et al., "High-Efficiency Gene Transfer into Normal and Adenosine Deaminase-Deficient T Lymphocytes Is Mediated by Transduction on Recombinant Fibronectin Fragments," *J. Virol.* 72(6):4882-4892 (1998).
Ponimaskin et al., "Sendai Virosomes Revisited: Reconstitution with Exogenous Lipids Leads to Potent Vehicles for Gene Transfer," *Virology* 269(2):391-403 (2000).
Prelle et al., "Establishment of Pluripotent Cell Lines from Vertebrate Species—Present Status and Future Prospects," *Cells Tissues Organs* 165(3-4):220-236 (1999).
Puls and Minchin, "Gene Transfer and Expression of a Non-Viral Polycation-Based Vector in CD4+ Cells," *Gene Ther.* 6(10):1774-1778 (1999).
Ramani et al., "Novel Gene Delivery to Liver Cells Using Engineered Virosomes," *FEBS Lett.* 404(2-3):164-168 (1997).
Reubinoff et al., "Embryonic Stem Cell Lines From Human Blastocysts: Somatic Differentiation In Vitro," *Nat. Biotechnol.* 18(4):399-404 (2000).
Rosenberg et al., "Gene Therapist, Heal Thyself," *Science* 287(5459):1751 (2000).

(56) References Cited

OTHER PUBLICATIONS

Rosenberg et al., "Gene Transfer Into Humans—Immunotherapy of Patients with Advanced Melanoma, Using Tumor-Infiltrating Lymphocytes Modified by Retroviral Gene Transduction," *N. Eng. J. Med.* 323(9):570-578 (1990).
Rudoll et al., "High-Efficiency Retroviral Vector Mediated Gene Transfer into Human Peripheral Blood CD4+ T Lymphocytes," *Gene Ther.* 3(8):695-705 (1996).
Russell, "Replicating Vectors for Gene Therapy of Cancer: Risks, Limitations and Prospects," *European J Cancer* 30A(8):1165-1171, 1994.
Sakai et al. "Accommodation of Foreign Genes into the Sendai Virus Genome: Sizes of Inserted Genes and Viral Replication," *FEBS Lett.* 456(2):221-226 (1999).
Sakurada et al., "Cloning, Expression, and Characterization of the *Micromonospora viridifaciens* Neuraminidase Gene in *Streptomyces lividans,"* *J. Bacteriol.* 174(21):6896-6903 (1992).
Sanderson et al., "Sendai Virus Assembly: M Protein Binds to Viral Glycoproteins in Transit through the Secretory Pathway," *J. Virol.* 67(2):651-663 (1993).
Sanderson et al., "Sendai Virus M Protein Binds Independently to Either the F or the HN Glycoprotein In Vivo," *J. Virol.* 68(1):69-76 (1994).
Schnell et al., "Development of a Self-Inactivating, Minimal Lentivirus Vector Based on Simian Immunodeficiency Virus," *Hum. Gene Ther.* 11 (3):439-447 (2000).
Schoch et al., "A Subset of Mouse Tracheal Epithelial Basal Cells Generates Large Colonies In Vitro," *Am. J. Physiol. Lung. Cell Mol. Physiol.* 286(4):L631-L642 (2004). E-published on Sep. 5, 2003.
Schwartz et al., "Synthetic DNA-Compacting Peptides Derived from Human Sequence Enhance Cationic Lipid-Mediated Gene Transfer In Vitro and In Vivo," *Gene Ther.* 6(2):282-292 (1999).
Shiotani et al. "Skeletal Muscle Regeneration After Insulin-Like Growth Factor I Gene Transfer by Recombinant Sendai Virus Vector," *Gene Ther.* 8(14):1043-1050 (2001).
Simons and Ikonen, "Functional Rafts in Cell Membranes," *Nature* 387(6633):569-572 (1997).
Sinn et al., "Persistent Gene Expression in Mouse Nasal Epithelia Following Feline Immunodeficiency Virus-Based Vector Gene Transfer," *J. Virol.* 79(20):12818-12827 (2005).
Speilhofer et al., "Chimeric Measles Viruses with a Foreign Envelope," *J. Virol.* 72(3):2150-2159 (1998).
Spiegel et al., "Asialoglycoprotein (ASGP-R)-Restricted Gene Transfer by Retroviral Particles Pseudotyped with Sendai Virus F Protein," *Hepatology* (Abstract 1429) 28:520A (1998).
Spiegel et al., "Pseudotype Formation of Moloney Murine Leukemia Virus with Sendai Virus Glycoprotein F," *J. Virol.* 72(6):5296-5302 (1998).
Stockschläder et al., "Expansion and Fibronectin-Enhanced Retroviral Transduction of Primary Human T Lymphocytes for Adoptive Immunotherapy," *J. Hematother. Stem Cell Res.* 8(4):401-410 (1999).
Storey et al., "Nucleotide Sequence of the Coding and Flanking Regions of the Human Parainfluenza Virus 3 Hemagglutinin—Neuraminidase Gene: Comparison with Other Paramyxoviruses," *Intervirology* 27(2):69-80 (1987).
Stricker and Roux, "The Major Glycoprotein of Sendai Virus Is Dispensable for Efficient Virus Particle Budding," *J. Gen. Virol.* 72(Pt. 7):1703-1707 (1991).
Suemori et al., "Establishment of Embryonic Stem Cell Lines from Cynomolgus Monkey Blastocysts Produced by IVF or ICSI," *Dev. Dyn.* 222(2):273-279 (2001).
Sun et al., "Neuraminidase from a Bacterial Source Enhances Both HIV-1-Mediated Syncytium Formation and the Virus Binding/Entry Process," *Virology* 284(1):26-36 (2001).
Thomas et al, "Progress and problems with the use of viral vectors for gene therapy," *Nature* 346(4):346-358, May 2003.
Thompson and Portner, "Localization of Functional Sites on the Hemagglutinin-Neuraminidase Glycoprotein of Sendai Virus by Sequence Analysis of Antigenic and Temperature-Sensitive Mutants," *Virology* 160(1):1-8 (1987).
Thomson and Marshall, "Primate Embryonic Stem Cells," *Curr. Top. Dev. Biol.* 38:133-165 (1998).
Thomson et al., "Embryonic Stem Cell Lines Derived From Human Blastocysts," *Science* 282(5391):1145-1147 (1998).
Thomson et al., "Isolation of a Primate Embryonic Stem Cell Line," *Proc. Natl. Acad. Sci. USA* 92(17):7844-7848 (1995).
Tomasi et al., "Conjugation of Specific Antibodies to Sendai Virus Particles," *FEBS Lett.* 143(2):252-256 (1982).
Toneguzzo and Keating, "Stable Expression of Selectable Genes Introduced into Human Hematopoietic Stem Cells by Electric Field-Mediated DNA Transfer," *Proc. Natl. Acad. Sci. USA* 83(10):3496-3499 (1986).
Torii et al., "Establishment of the Primate Embryonic Stem Cell Lines from Blastocysts Produced by Intra Cytoplasmic Sperm Injection (ICSI) or In Vitro Fertilization (IVF) Using the Japanese Monkey and Cynomolgus Monkey," *Theriogenology* 55:Abstract 374 (2001).
Touchette "Gene Therapy: Not Ready for Prime Time," *Nat. Med.* 2(1):7-8 (1996).
Tuffereau et al., "The Role of Haemagglutinin-Neuraminidase Glycoprotein Cell Surface Expression in the Survival of Sendai Virus-Infected BHK-21 Cells," *J. Gen. Virol.* 66 (Pt. 11):2313-2318 (1985).
Tuohy and Mathisen, "T Cell Design for Therapy in Autoimmune Demyelinating Disease," *J. Neuroimmunol.* 107(2):226-232 (2000).
Uchida et al., "High Efficiency Gene Transfer into Murine T Cell Clones Using a Retroviral Vector," *J. Immunol.* 136(5):1876-1879 (1986).
Verma et al., "Gene Therapy—promises, problems and prospects," *Nature* 389:239-242, 1997.
Vzorov and Compans, "Effect of the Cytoplasmic Domain of the Simian Immunodeficiency Virus Envelope Protein on Incorporation of Heterologous Envelope Proteins and Sensitivity to Neutralization," *J. Virol.* 74(18):8219-8225 (2000).
Wagner et al., "Effects of Anionic and Nonionic Polymers on Fusion and Binding of Sendai Virus to Human Erythrocyte Ghosts," *Antivir. Res.* 39(2):113-127 (1998).
Wickham et al., "Targeted Adenovirus-Mediated Gene Delivery to T Cells Via CD3," *J. Virol.* 71 (10):7663-7669 (1997).
Williams et al., "Myeloid Leukaemia Inhibitory Factor Maintains the Developmental Potential of Embryonic Stem Cells," *Nature* 336(6200):684-687 (1988).
Xu et al., "Feeder-Free Growth of Undifferentiated Human Embryonic Stem Cells," *Nat. Biotechnol.* 19(10):971-974 (2001).
Yang et al., "Hemagglutinin Specificity and Neuraminidase Coding Capacity of Neuraminidase-Deficient Influenza Viruses," *Virology* 229(1):155-165 (1997).
Yonemitsu et al., "Efficient Gene Transfer to Airway Epithelium Using Recombinant Sendai Virus," *Nat. Biotechnol.* 18(9):970-973 (2000).
Yoshida et al., "Membrane (M) Protein of HVJ (Sendai Virus): Its Role in Virus Assembly," *Virology* 71(1):143-161 (1976).
Yu et al., "Sendai Virus-Based Expression of HIV-1 gp120: Reinforcement by the V(-) Version," *Genes to Cells* 2(7):457-466 (1997).
Zeitlin et al., "Alveolar Stem Cell Transduction by an Adeno-Associated Viral Vector," *Gene Ther.* 2(9): 623-631 (1995).
Zhirnov, "Solubilization of Matrix Protein M1/M from Virions Occurs at Different pH for Orthomyxo- and Paramyxoviruses," *Virology* 176(1):274-279 (1990).
Davies et al., "Prospects for gene therapy in lung disease," *Current Opinion in Pharmacology* 1:272-277 (2001).
Dunbar III et al., "Prolonged Survival in Hereditary Surfactant Protein B (SP-B) Deficiency Associated with a Novel Splicing Mutation," *Pediatric Research* 48(3):275-282 (2000).
Lahti et al., "Surfactant protein C gene variation in the Finnish population—association with perinatal respiratory disease," *European Journal of Human Genetics* 12:312-320 (2004).

(56) References Cited

OTHER PUBLICATIONS

Nogee et al., "A Mutation in the Surfactant Protein B Gene Responsible for Fatal Neonatal Respiratory Disease in Multiple Kindreds," *J. Clin. Invest.* 93:1860-1863 (Apr. 1994).

* cited by examiner

FIG. 1

SIVct/HN <u>*WSELKIRSNDGGEGPEDANDPRGKGVQHIHIQPSLPVYGQRVRVR*</u> *WLLILSFTQ*

(SEQ ID NO: 1)

<u>*XXX*</u>: SIV CYTOPLASMIC DOMAIN *XXX*: HN PROTEIN TRANSMEMBRANE DOMAIN

FIG. 2

SIVct+HN *WSELKIRSNDGGEGPEDANDPRGKGVQHIHIQPSLPVYGQRVRVR* DGDRGKRDS
(SEQ ID NO: 2)

*XXX*: SIV CYTOPLASMIC DOMAIN XXX: HN PROTEIN CYTOPLASMIC DOMAIN

FIG. 3

$F_{ct\ 4}$ *VVIIVIIIVLY*RLRR (SEQ ID NO: 3)
4

$F_{ct14}$ *VVIIVIIIVLY*RLRRSMLMGNPDDR (SEQ ID NO: 4)
14

$F_{ct27}$ *VVIIVIIIVLY*RLRRSMLMGNPDDRIPRDTYTLEPKIR
27
(SEQ ID NO: 5)

*XXX*: F PROTEIN TRANSMEMBRANE DOMAIN
XXX: F PROTEIN CYTOPLASMIC DOMAIN

FIG. 4

$F_{ct\ 4}/SIV_{ct11}$ *VVIIVIIIVL* *Y*RLRR *__RVRQGYVPLSP__* (SEQ ID NO: 6)

$F_{ct14}/SIV_{ct11}$ *VVIIVIIIVL* *Y*RLRRSMLMGNPDDR *__RVRQGYVPLSP__* (SEQ ID NO: 7)

$F_{ct27}/SIV_{ct11}$ *VVIIVIIIVL* *Y*RLRRSMLMGNPDDRIPRDTYTLEPKIR *__RVRQGYVPLSP__* (SEQ ID NO: 8)

*XXX*: F PROTEIN TRANSMEMBRANE DOMAIN

XXX: F PROTEIN CYTOPLASMIC DOMAIN

*__XXX__*: 11 AMINO ACIDS OF SIV CYTOPLASMIC DOMAIN ($SIV_{ct11}$)

SEQUENCE LISTING

```
<160> NUMBER OF SEQ ID NOS: 17

<210> SEQ ID NO 1
<211> LENGTH: 54
<212> TYPE: PRT
<213> ORGANISM: Artificial
```

-continued

```
<220> FEATURE:
<223> OTHER INFORMATION: artificially synthesized sequence

<400> SEQUENCE: 1

Trp Ser Glu Leu Lys Ile Arg Ser Asn Asp Gly Gly Glu Gly Pro Glu
1               5                   10                  15

Asp Ala Asn Asp Pro Arg Gly Lys Gly Val Gln His Ile His Ile Gln
            20                  25                  30

Pro Ser Leu Pro Val Tyr Gly Gln Arg Val Arg Val Arg Trp Leu Leu
        35                  40                  45

Ile Leu Ser Phe Thr Gln
    50


<210> SEQ ID NO 2
<211> LENGTH: 54
<212> TYPE: PRT
<213> ORGANISM: Artificial
<220> FEATURE:
<223> OTHER INFORMATION: artificially synthesized sequence

<400> SEQUENCE: 2

Trp Ser Glu Leu Lys Ile Arg Ser Asn Asp Gly Gly Glu Gly Pro Glu
1               5                   10                  15

Asp Ala Asn Asp Pro Arg Gly Lys Gly Val Gln His Ile His Ile Gln
            20                  25                  30

Pro Ser Leu Pro Val Tyr Gly Gln Arg Val Arg Val Arg Asp Gly Asp
        35                  40                  45

Arg Gly Lys Arg Asp Ser
    50


<210> SEQ ID NO 3
<211> LENGTH: 15
<212> TYPE: PRT
<213> ORGANISM: Artificial
<220> FEATURE:
<223> OTHER INFORMATION: artificially synthesized sequence

<400> SEQUENCE: 3

Val Val Ile Ile Val Ile Ile Ile Val Leu Tyr Arg Leu Arg Arg
1               5                   10                  15


<210> SEQ ID NO 4
<211> LENGTH: 25
<212> TYPE: PRT
<213> ORGANISM: Artificial
<220> FEATURE:
<223> OTHER INFORMATION: artificially synthesized sequence

<400> SEQUENCE: 4

Val Val Ile Ile Val Ile Ile Ile Val Leu Tyr Arg Leu Arg Arg Ser
1               5                   10                  15

Met Leu Met Gly Asn Pro Asp Asp Arg
            20                  25


<210> SEQ ID NO 5
<211> LENGTH: 38
<212> TYPE: PRT
<213> ORGANISM: Artificial
<220> FEATURE:
<223> OTHER INFORMATION: artificially synthesized sequence

<400> SEQUENCE: 5

Val Val Ile Ile Val Ile Ile Ile Val Leu Tyr Arg Leu Arg Arg Ser
```

-continued

```
1               5                   10                  15

Met Leu Met Gly Asn Pro Asp Asp Arg Ile Pro Arg Asp Thr Tyr Thr
            20                  25                  30

Leu Glu Pro Lys Ile Arg
        35


<210> SEQ ID NO 6
<211> LENGTH: 26
<212> TYPE: PRT
<213> ORGANISM: Artificial
<220> FEATURE:
<223> OTHER INFORMATION: artificially synthesized sequence

<400> SEQUENCE: 6

Val Val Ile Ile Val Ile Ile Ile Val Leu Tyr Arg Leu Arg Arg Arg
1               5                   10                  15

Val Arg Gln Gly Tyr Val Pro Leu Ser Pro
            20                  25


<210> SEQ ID NO 7
<211> LENGTH: 36
<212> TYPE: PRT
<213> ORGANISM: Artificial
<220> FEATURE:
<223> OTHER INFORMATION: artificially synthesized sequence

<400> SEQUENCE: 7

Val Val Ile Ile Val Ile Ile Ile Val Leu Tyr Arg Leu Arg Arg Ser
1               5                   10                  15

Met Leu Met Gly Asn Pro Asp Asp Arg Arg Val Arg Gln Gly Tyr Val
            20                  25                  30

Pro Leu Ser Pro
        35


<210> SEQ ID NO 8
<211> LENGTH: 49
<212> TYPE: PRT
<213> ORGANISM: Artificial
<220> FEATURE:
<223> OTHER INFORMATION: artificially synthesized sequence

<400> SEQUENCE: 8

Val Val Ile Ile Val Ile Ile Ile Val Leu Tyr Arg Leu Arg Arg Ser
1               5                   10                  15

Met Leu Met Gly Asn Pro Asp Asp Arg Ile Pro Arg Asp Thr Tyr Thr
            20                  25                  30

Leu Glu Pro Lys Ile Arg Arg Val Arg Gln Gly Tyr Val Pro Leu Ser
        35                  40                  45

Pro


<210> SEQ ID NO 9
<211> LENGTH: 34
<212> TYPE: DNA
<213> ORGANISM: Artificial
<220> FEATURE:
<223> OTHER INFORMATION: an artificially synthesized primer sequence

<400> SEQUENCE: 9

gagactcgag atgtggtctg agttaaaaat cagg                                 34


<210> SEQ ID NO 10
<211> LENGTH: 63
```

-continued

```
<212> TYPE: DNA
<213> ORGANISM: Artificial
<220> FEATURE:
<223> OTHER INFORMATION: an artificially synthesized primer sequence

<400> SEQUENCE: 10

agaggtagac cagtacgagt cacgtttgcc cctatcacca tccctaaccc tctgtccata     60

aac                                                                   63


<210> SEQ ID NO 11
<211> LENGTH: 31
<212> TYPE: DNA
<213> ORGANISM: Artificial
<220> FEATURE:
<223> OTHER INFORMATION: an artificially synthesized primer sequence

<400> SEQUENCE: 11

ccgctcgagc atgacagcat atatccagag a                                    31


<210> SEQ ID NO 12
<211> LENGTH: 40
<212> TYPE: DNA
<213> ORGANISM: Artificial
<220> FEATURE:
<223> OTHER INFORMATION: an artificially synthesized primer sequence

<400> SEQUENCE: 12

atagtttagc ggccgctcat ctgatcttcg gctctaatgt                           40


<210> SEQ ID NO 13
<211> LENGTH: 40
<212> TYPE: DNA
<213> ORGANISM: Artificial
<220> FEATURE:
<223> OTHER INFORMATION: an artificially synthesized primer sequence

<400> SEQUENCE: 13

atagtttagc ggccgctcaa cggtcatctg gattacccat                           40


<210> SEQ ID NO 14
<211> LENGTH: 40
<212> TYPE: DNA
<213> ORGANISM: Artificial
<220> FEATURE:
<223> OTHER INFORMATION: an artificially synthesized primer sequence

<400> SEQUENCE: 14

atagtttagc ggccgctcac cttctgagtc tataaagcac                           40


<210> SEQ ID NO 15
<211> LENGTH: 73
<212> TYPE: DNA
<213> ORGANISM: Artificial
<220> FEATURE:
<223> OTHER INFORMATION: an artificially synthesized primer sequence

<400> SEQUENCE: 15

atagtttagc ggccgcctat ggagatagag gaacatatcc ctgcctaacc cttctgatct     60

tcggctctaa tgt                                                        73


<210> SEQ ID NO 16
<211> LENGTH: 73
<212> TYPE: DNA
<213> ORGANISM: Artificial
<220> FEATURE:
```

-continued

```
<223> OTHER INFORMATION: an artificially synthesized primer sequence

<400> SEQUENCE: 16

atagtttagc ggccgcctat ggagatagag gaacatatcc ctgcctaacc ctacggtcat     60

ctggattacc cat                                                        73


<210> SEQ ID NO 17
<211> LENGTH: 73
<212> TYPE: DNA
<213> ORGANISM: Artificial
<220> FEATURE:
<223> OTHER INFORMATION: an artificially synthesized primer sequence

<400> SEQUENCE: 17

atagtttagc ggccgcctat ggagatagag gaacatatcc ctgcctaacc ctccttctga     60

gtctataaag cac                                                        73
```

GENE TRANSFER INTO AIRWAY EPITHELIAL STEM CELL BY USING LENTIVIRAL VECTOR PSEUDOTYPED WITH RNA VIRUS OR DNA VIRUS SPIKE PROTEIN

The present application is a continuation of U.S. application Ser. No. 12/091,646, filed Nov. 10, 2008, now abandoned, which is a 371 filing of PCT/JP2006/32157 filed Oct. 27, 2006 which claims benefit to Japanese application 2005-313971 filed Oct. 28, 2005.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 270077_401C1_SEQUENCE_LISTING.txt. The text file is 6 KB, was created on Feb. 4, 2015, and is being submitted electronically via EFS-Web.

TECHNICAL FIELD

The present invention relates to lentiviral vectors pseudotyped with RNA or DNA virus spike proteins for introducing genes into airway epithelial stem cells.

BACKGROUND ART

Cystic fibrosis (CF) is the most common lethal autosomal recessive disorder among Caucasians. It is caused by mutations in the CF transmembrane conductance regulator (CFTR) gene. Such mutations prevent ion transfer across the airway epithelium, which leads to mucosal thickening and attachment of bacteria, ultimately causing the disorder. Therefore, airway epithelial cells are important targets for gene therapy.

For long-term expression of transgenes, it is important to introduce genes into airway epithelial progenitor cells including stem cells. "Stem cells" refers to undifferentiated cells which are multipotent and capable of self-renewal. In the case of the airway, stem cells are present near the ductal epithelia of the sub-mucosal glands and the basal cells of the basement membrane, and the ductal epithelium and the basal cells are protected from external toxins and injuries (see Non-patent Documents 1 and 2). Furthermore, in the mouse trachea, they are also reported to be scattered in the cartilage tissue (see Non-patent Document 1). In general, since epithelial stem cells are very few in number and exist in isolated locations in the sub-mucosal glands, it is difficult to adopt the gene transfer approach and such. Furthermore, it is known that airway epithelial cells including stem cells are tissues where gene transfer is very difficult due to the presence of the mucin layer and mucus.

Moreover, airway epithelial cells have polarity, and the side in contact with outside air is referred to as apical side, and the celomic side is referred to as basolateral side. Since there are no virus receptors on the apical surface of airway epithelial cells, there are hardly any vectors that can be efficiently transduced into intact airway epithelium. Receptors for most viruses including adenovirus are present on the basolateral side; therefore, preconditioning using EGTA, surfactants and such is necessary immediately before gene transfer. In the case of lentiviral vectors pseudotyped with vesicular stomatitis virus glycoprotein (VSV-G), for example, the epithelial surface must be preconditioned with a detergent to perform efficient transfection. However, clinically it may not be possible to use treatment with these chemical substances.

Vectors for gene therapy and methods for their administration are being developed for genetic diseases of impaired respiratory system, such as cystic fibrosis. For gene transfer into airway epithelial cells, it is necessary to introduce the gene from the apical side of the epithelial cells by passing through the mucin layer and mucus. Invasion of virus vectors that infect from the basolateral side is blocked by tight junctions present between epithelial cells. Accordingly, administration methods that disrupt these tight junctions by the combined use of a calcium chelating agent, EGTA, and various surfactants are employed. However, such treatments (preconditioning) are not desirable for clinical application to humans.

Since VSV-G receptors that are generally used for pseudotyping are present on the basolateral side of airway epithelial cells, treatment with lysophosphatidylcholine (LPC; a type of surfactant) is necessary for gene transfer. When a mouse nasal cavity was infected with a VSV-G-pseudotyped HIV vector (carried gene; lacZ) after LPC treatment, the transgene expression was maintained for at least 92 days (see Non-patent Document 3). The result suggests the gene has been introduced into stem cells because epithelial cells lived three months. As an example of lentiviral vector pseudotyping without preconditioning, an envelope protein of the Ebola virus Zaire strain has been reported (see Non-patent Document 4). The carried gene LacZ was found to be maintained for 63 days in the mouse airway tissues. Although the duration of this experiment was shorter than the survival time of epithelial cells, the gene was confirmed to be transferred into the sub-mucosal gland where the stem cells are said to exist.

The following documents are also known.

[Non-patent Document 1] Borthwick et al., Am J. Respir. Cell Mol. Biol., Vol. 24, pp. 662-670, 2001

[Non-patent Document 2] Engelhardt, Am J. Respir. Cell Mol. Biol., Vol. 24, pp. 649-652, 2001

[Non-patent Document 3] Limberis, et al., Human Gene Therapy, Vol. 13, pp. 1961-1970, 2002

[Non-patent Document 4] Kobinger et al., Nature Biotechnology, Vol. 19, pp. 225-230, 2001

[Non-patent Document 5] Alberto Auricchio et al., The Journal of Clinical Investigation, Vol. 110, Number 4, pp. 499-504, 2002

[Non-patent Document 6] John F. Engelhardt, The Journal of Clinical Investigation, Vol. 110, Number 4, pp. 429-432, 2002

DISCLOSURE OF THE INVENTION

Problems to be Solved by the Invention

An objective of the present invention is to provide lentiviral vectors pseudotyped with RNA or DNA virus spike proteins for introducing genes into airway epithelial stem cells.

Means for Solving the Problems

The present inventors carried out dedicated research to solve the above-mentioned problems. Specifically, to develop vectors that can introduce genes into airway epithelial stem cells, vectors of a simian immunodeficiency virus (SIV), a type of lentivirus, were pseudotyped with envelope glycoproteins F and HN, which are spike proteins of Sendai virus, a type of RNA virus.

The airway epithelium is covered with mucus, and it has been difficult to transfer genes into airway epithelial cells and such with conventional techniques. For introducing genes into these cells, a method that physically removes the extracellular matrix such as mucus by washing had been tried. However, this method was cumbersome and posed the danger of tissue damage.

This time, the present inventors focused on the function of Sendai virus, a virus infecting the airway system, to efficiently transfect from the apical side airway epithelial cells that have not been preconditioned; developed vectors produced by pseudotyping a simian immunodeficiency virus vector with Sendai virus envelope glycoproteins F and HN; and for the first time, discovered methods of using these vectors to introduce genes into airway epithelial cells and airway stem cells.

Lentiviral vectors such as simian immunodeficiency virus vectors incorporate a carried gene into host genome by the action of an integrase. Therefore, if genes can be introduced into stem cells using a simian immunodeficiency virus vector pseudotyped with Sendai virus glycoproteins, the vectors will be useful for treating genetic diseases of the respiratory system, such as cystic fibrosis.

As described above, the present inventors developed vectors produced by pseudotyping simian immunodeficiency virus vectors with glycoproteins F and HN which are spike proteins of the airway-infecting Sendai virus; and developed methods of using these vectors for efficiently introducing genes into airway epithelial stem cells without preconditioning, from the apical side through the mucus layer. By using glycoproteins of airway-infecting viruses as envelope proteins, it became possible to introduce genes into airway epithelial cells as well as stem cells including progenitor cells. The technique for introducing genes into stem cells using the vectors of the present invention enables stable maintenance of gene expression, well beyond the survival time of epithelial cells.

Specifically, the present invention relates to lentiviral vectors pseudotyped with RNA or DNA virus spike proteins for introducing genes into airway epithelial stem cells, and more specifically relates to the following:

[1] a lentiviral vector for introducing a gene into an airway epithelial stem cell, wherein the vector is pseudotyped with an RNA or DNA virus spike protein;

[2] the lentiviral vector of [1], wherein the RNA virus is an RNA virus that infects an airway tissue;

[3] the lentiviral vector of [1], wherein the RNA virus is a minus-strand RNA virus;

[4] the lentiviral vector of [3], wherein the minus-strand RNA virus is a paramyxovirus;

[5] the lentiviral vector of [4], wherein the paramyxovirus is Sendai virus;

[6] the lentiviral vector of [3], wherein the minus-strand RNA virus is an orthomyxovirus;

[7] the lentiviral vector of [6], wherein the orthomyxovirus is an influenza virus;

[8] the lentiviral vector of [3], wherein the minus-strand RNA virus is a filovirus;

[9] the lentiviral vector of [8], wherein the filovirus is Ebola hemorrhagic fever virus;

[10] the lentiviral vector of [1], wherein the RNA virus is a plus-strand RNA virus;

[11] the lentiviral vector of [10], wherein the plus-strand RNA virus is a coronavirus;

[12] the lentiviral vector of [11], wherein the coronavirus is SARS coronavirus;

[13] the lentiviral vector of [1], wherein the DNA virus is a DNA virus that infects an airway tissue;

[14] the lentiviral vector of [13], wherein the DNA virus is a baculovirus;

[15] the lentiviral vector of any one of [1] to [14], wherein the lentiviral vector is a recombinant simian immunodeficiency virus vector;

[16] the lentiviral vector of [15], wherein the recombinant simian immunodeficiency virus vector is derived from an agm strain;

[17] the lentiviral vector of [15] or [16], wherein the recombinant simian immunodeficiency virus vector is a self-inactivating vector;

[18] the lentiviral vector of any one of [1] to [14], wherein the lentiviral vector is an equine infectious anemia virus vector, human immunodeficiency virus-1 vector, human immunodeficiency virus-2 vector, or feline immunodeficiency virus vector;

[19] the lentiviral vector of any one of [1] to [18], which carries a foreign gene in an expressible state;

[20] the lentiviral vector of [19], wherein the foreign gene is a gene encoding a protein selected from the green fluorescent protein, beta-galactosidase, and luciferase;

[21] the lentiviral vector of [19], wherein the foreign gene is a gene encoding an inherent or acquired dysfunctional protein;

[22] the lentiviral vector of [19], wherein the foreign gene is a gene encoding an inherent or acquired dysfunctional cystic fibrosis (CF)-causing factor;

[23] the lentiviral vector of [19], wherein the foreign gene is a gene encoding an inherent or acquired dysfunctional CFTR (cystic fibrosis transmembrane conductance regulator) protein;

[24] the lentiviral vector of [19], wherein the foreign gene is a gene encoding a protein having a therapeutic effect on cystic fibrosis;

[25] the lentiviral vector of [19], wherein the foreign gene is a gene encoding a protein that has become dysfunctional due to a genetic disease;

[26] the lentiviral vector of [25], wherein the protein that has become dysfunctional due to a genetic disease is a gene encoding CFTR;

[27] a method for introducing a gene into an airway epithelial stem cell, which comprises the step of contacting an airway epithelial cell with the lentiviral vector of any one of [1] to [26];

[28] an airway epithelial stem cell into which the lentiviral vector of any one of [1] to [26] has been introduced;

[29] an agent for transferring a gene into an airway epithelial stem cell, which comprises the lentiviral vector of any one of [1] to [26] as an active ingredient;

[30] the agent of [29], wherein the lung is used as a production tissue to provide a protein necessary for disease treatment;

[31] a therapeutic agent for genetic respiratory disease, which comprises the lentiviral vector of any one of [1] to [26] as an active ingredient; and

[32] the therapeutic agent of [31], wherein the genetic respiratory disease is cystic fibrosis.

Furthermore, the present invention relates to methods for preventing or treating genetic respiratory diseases, which comprise the step of administering a lentiviral vector of the present invention to an individual. The present invention also relates to prevention or treatment methods in which the above-mentioned genetic respiratory disease is cystic fibrosis. Furthermore, the present invention relates to uses of lentiviral vectors of the present invention for producing therapeutic agents for genetic respiratory diseases. The present invention also relates to their use for producing therapeutic agents, in which the above-mentioned genetic respiratory disease is cystic fibrosis.

BRIEF DESCRIPTION OF THE DRAWINGS

FIG. 1 depicts the amino acid sequence (SEQ ID NO: 1) of the boundary portion between the SIV cytoplasmic domain (underlined portion in italics) and the HN protein transmembrane domain (in italics) of a protein encoded by a cytoplasmic domain-substituted HN expression plasmid.

FIG. 2 depicts the amino acid sequence (SEQ ID NO: 2) of the boundary portion between the cytoplasmic domain (underlined portion in italics) and the HN protein transmembrane domain (in standard style) of a protein encoded by an SIV cytoplasmic domain-added HN expression plasmid.

FIG. 3 depicts the amino acid sequences (SEQ ID NOs: 3 to 5) of the boundary portion between the F protein transmembrane domain (in italics) and the F protein cytoplasmic domain (in standard style) of proteins encoded by cytoplasmic domain-deleted F expression plasmids.

FIG. 4 depicts the amino acid sequences (SEQ ID NOs: 6 to 8) of the boundary portion of the F protein transmembrane domain (in italics without underline), F protein cytoplasmic domain (in standard style), and 11 amino acids of the SIV cytoplasmic domain ($SIV_{c11}$) (underlined portion in italics) of proteins encoded by cytoplasmic domain-deleted F expression plasmid to which the SIV cytoplasmic domain has been added.

BEST MODE FOR CARRYING OUT THE INVENTION

Figure 5:
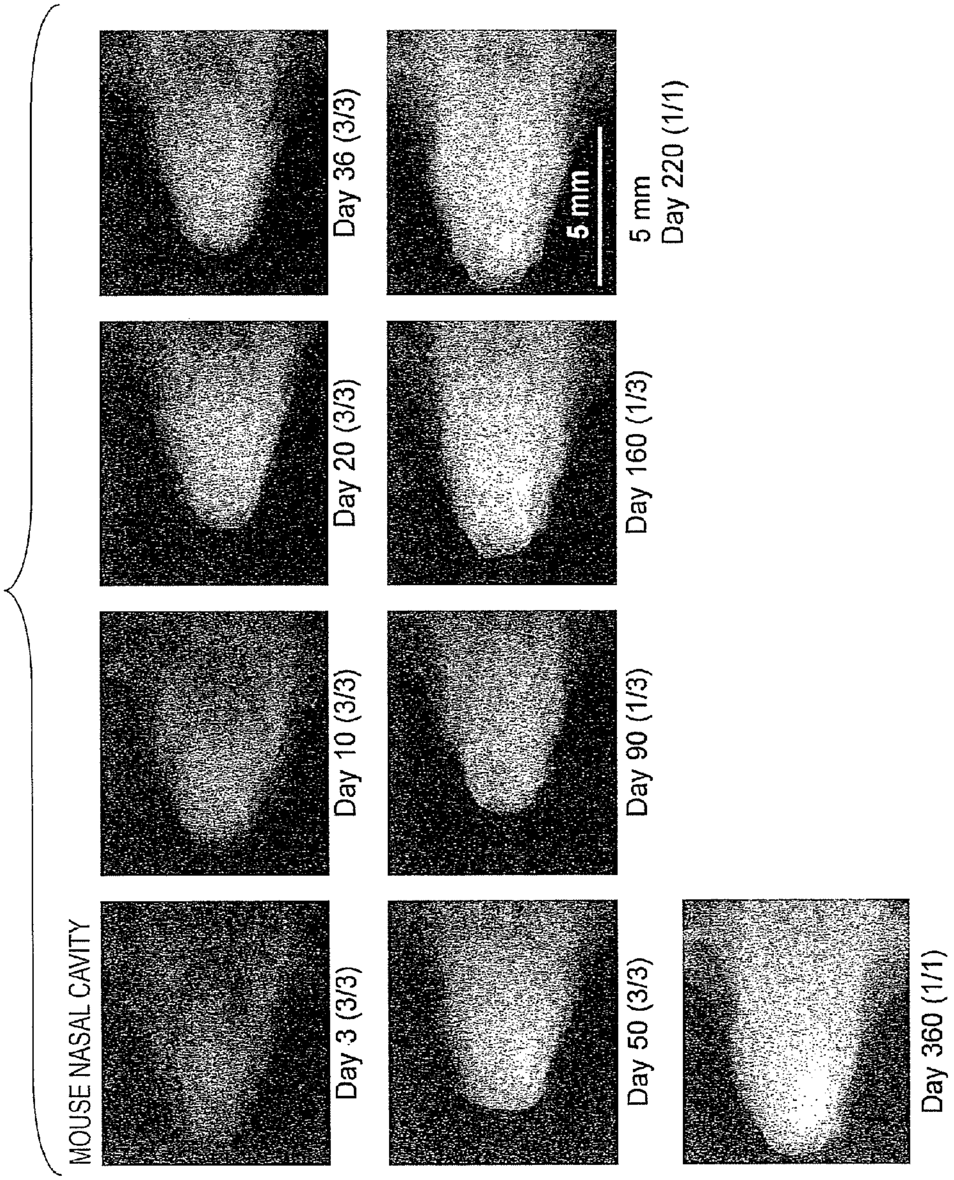
FIG. 5 shows photographs indicating long-term gene expression in the mouse nasal cavity by an F/HN-pseudotyped SIV vector of the present invention. The results of day 3 to day 360 are shown. The numbers in parentheses (x/x) indicate the number of mouse individuals showing gene expression/number of mouse individuals tested. When the numerical values are separated on the left and right, the left shows the number of individuals indicating strong GFP expression, and the right shows the number of mouse individuals used for analysis each day. The scale bar represents 5 mm.

The present inventors constructed vectors pseudotyped with spike proteins of minus-strand RNA viruses by using a simian immunodeficiency virus (SIV) selected from lentiviruses expected to be used as a gene therapy vector. The simian immunodeficiency virus has various advantages such as high safety compared to the human immunodeficiency virus (HIV) conventionally used in the field of gene therapy. For example, simian immunodeficiency virus vectors pseudotyped with the F and RN proteins of Sendai virus, a minus-strand RNA virus, were constructed as described below in the Examples. Furthermore, foreign genes were successfully introduced into stem cells of the mouse nasal cavity by using these vectors.

More specifically, the present invention provides lentiviral vectors pseudotyped with RNA virus or DNA virus spike proteins (herein below, these vectors may be referred to as "pseudotyped lentiviral vectors" or simply "vectors") for introducing genes into airway epithelial stem cells.

"Lentiviral vectors" of the present invention are virus particles that contain a lentivirus-derived viral genome, lack the self-renewal ability, and have the ability to introduce a nucleic acid molecule into a host. Specifically, these vectors have a lentiviral backbone. The phrase "has a lentiviral backbone" means that the nucleic acid molecule included in the virus particles constituting the vectors is based on a lentiviral genome. For example, the lentiviral vectors of the present invention include vectors in which a nucleic acid molecule contained in virus particles contains a lentiviral genome-derived packaging signal sequence. Furthermore, "recombinant viral vectors" in the present invention refers to viral vectors constructed by genetic recombination techniques. Viral vectors constructed using packaging cells and DNAs encoding a viral genome are called recombinant viral vectors.

"Lentiviruses" refers to retroviruses belonging to the lentivirus subfamily. Viruses such as the following are included as lentiviruses:

human immunodeficiency virus (HIV) (for example, HIV1 or HIV2);

simian immunodeficiency virus (SIV);

feline immunodeficiency virus (FIV);

Maedi-Visna-like virus (EV1);

equine infectious anemia virus (EIAV); and caprine arthritis encephalitis virus (CAEV).

In the present invention, lentiviral vectors derived from any strain and subtype can be used. For example, as HIV1, all major (M) subtypes (including A to J), N, and outliers (O) are included (Hu, D. J. et al., JAMA 1996; 275: 210-216; Zhu, T. et al., Nature 1998, 5; 391 (6667): 594-7; Simon, F. et al., Nat. Med. 1998, 4 (9): 1032-7).

The phrase "lentiviral vectors pseudotyped with RNA virus spike proteins" refers to lentiviral vectors containing RNA virus spike proteins. It also refers to lentiviral vectors carrying one or more RNA virus spike proteins that are not carried by the natural form of the lentiviral vectors. The phrase "lentiviral vectors pseudotyped with DNA virus spike proteins" refers to lentiviral vectors containing DNA virus spike proteins. It also refers to lentiviral vectors carrying one or more DNA virus spike proteins that are not carried by the natural form of the lentiviral vectors.

In the present invention, the term "airway epithelial stem cell" which becomes a target of gene transfer refers to a stem cell present in airway epithelial tissues. Stem cells are undifferentiated cells that are multipotent and have the self-renewal ability. Three types are known: hematopoietic stem cells, mesenchymal stem cells (bone marrow stroma cells: D. J. Prockop, Science, 276, 71-74, 1997), and stem cells present in tissues of various organs. Furthermore, the term "airway epithelial tissues" refers to, for example, tissues of the nose, nasal cavity, pharynx, larynx, tracheae, bronchi, lungs and such. Preferred airway epithelial tissues in the present invention are the nasal cavity, tracheae, and lungs. Furthermore, airway epithelial stem cells of the present invention are not limited to stem cells present in the sub-mucosal glands. Specifically, airway epithelial stem cells can be defined as all hematopoietic stem cells, mesenchymal stem cells, and stem cells in various organ tissues that can differentiate into airway epithelial tissues.

The pseudotyped lentiviral vectors of the present invention have the function to introduce genes into airway epithelial stem cells. Specifically, RNA viruses or DNA viruses used for pseudotyping in the present invention preferably have the function to infect airway epithelial tissues.

In the present invention, the term "RNA virus" refers to a virus containing an RNA genome. RNA viruses in the present invention are preferably viruses that synthesize RNAs during their lifecycle using RNAs as a template. RNA viruses may be desirable RNA viruses that replicate genomic RNAs in airway epithelial cells, and they may be wild-type viruses, or mutant viruses such as attenuated viruses, temperature-sensitive viruses and such. Furthermore, they may be natural viruses (naturally occurring viruses) or recombinant viruses. RNA viruses include single-stranded RNA viruses (including plus-strand RNA viruses and minus-strand RNA viruses) and double-stranded RNA viruses. They also include viruses with envelope (enveloped viruses) and viruses without envelope (non-enveloped viruses), but preferably, enveloped viruses are used. RNA viruses in the present invention specifically include viruses belonging to the following families:

Arenaviridae such as Lassa virus;

Orthomyxoviridae such as influenza virus;

Coronaviridae such as SARS coronavirus;

Togaviridae such as rubella virus;

Paramyxoviridae such as mumps virus, measles virus, Sendai virus, and RS virus;

Picornaviridae such as poliovirus, Coxsackie virus, and echovirus;

Filoviridae such as Marburg virus and Ebola hemorrhagic fever virus;

Flaviviridae such as yellow fever virus, dengue fever virus, hepatitis C virus, and hepatitis G virus;

Bunyaviridae;

Rhabdoviridae such as rabies virus; and

Reoviridae.

The term "plus-strand RNA viruses" in the present invention refers to viruses that contain plus-strand RNAs as genome. Of them, SARS coronavirus (Severe Acute Respiratory Syndrome virus (SARS virus) and new type coronaviruses) of Coronaviridae are preferably used in the present invention. Plus-strand RNA viruses in the present invention include, for example, the following:

Coronaviridae such as SARS virus;

Caliciviridae such as norovirus;

Picornaviridae;

Astroviridae such as astrovirus;

Togaviridae;

Flaviviridae;

Retroviridae such as human immunodeficiency virus; and

Bunyaviridae.

Furthermore, the term "minus-strand RNA virus" in the present invention refers to a virus containing a minus strand (an antisense strand of a viral protein-encoding sense strand) RNA as genome. A minus-strand RNA is also referred to as a negative-strand RNA. The minus-strand RNA viruses used in the present invention particularly include single-stranded minus-strand RNA viruses (also referred to as non-segmented minus-strand RNA viruses). The term "single-stranded negative-strand RNA virus" refers to a virus containing a single-stranded negative-strand (i.e., minus-strand) RNA as genome.

The above-mentioned minus-strand RNA viruses include viruses belonging to Paramyxoviridae (including the genera Paramyxovirus, Morbillivirus, Rubulavirus, and Pneumovirus), Rhabdoviridae (including the genera Vesiculovirus, Lyssavirus, and Ephemerovirus), Filoviridae including Ebola hemorrhagic fever virus, Orthomyxoviridae (including Influenza viruses A, B, and C, and Thogoto-like viruses), Bunyaviridae (including the genera Bunyavirus, Hantavirus, Nairovirus, and Phlebovirus), Arenaviridae and the like.

Specific examples of minus-strand RNA viruses used in the present invention include Sendai virus, Newcastle disease virus, Mumps virus, Measles virus, Respiratory syncytial virus (RS virus), rinderpest virus, distemper virus, simian parainfluenza virus (SV5), and human parainfluenza viruses I, II, and III, which are Paramyxoviridae viruses; influenza virus belonging to Orthonzyxoviridae; the vesicular stomatitis virus and Rabies virus belonging to Rhabdoviridae; and Ebola virus belonging to Filoviridae. Of them, Sendai virus, influenza viruses, and Ebola viruses are preferably used in the present invention.

Sendai virus includes wild-type strain, mutant, laboratory-passaged strains, and artificially established strains. Defective viruses such as DI particles (J. Virol. 68, 8413-8417 (1994)), synthesized oligonucleotides and such may also be used as materials for producing pseudotyped lentiviral vectors of the present invention.

The "spike proteins" of the present invention may also be referred to as envelope proteins. Specifically, the term "spike proteins" refers to protruding proteins arranged on a virus envelope surface, which are virus glycoproteins and may exist as multimers. They play an indispensable role in the attachment and invasion of enveloped viruses into host cells. For example, the two types of spike proteins in Sendai virus are hemagglutinin-neuraminidase (HN) glycoprotein and fusion glycoprotein (F). In influenza virus, there are two types of spike proteins, hemagglutinin (trimer) (HA) and neuraminidase (tetramer) (NA). In SARS virus, spike glycoprotein exists as the spike protein. In the Ebola hemorrhagic fever virus Zaire strain, the EboZ envelope protein, a protruding protein of approximately 10 nm in length, exists as the spike protein.

Spike proteins of the present invention are not limited to the above-mentioned spike proteins such as HN, F, HA, NA, and EboZ; and for example, even if the names are different, proteins in other RNA viruses or DNA viruses that correspond to the above-mentioned spike proteins are also included in the present invention. These spike proteins may be modified by one or more amino acid substitutions, deletions, insertions, and/or additions to natural proteins, so long as the functions of the original proteins are maintained. The number of amino acids that can be modified is not particularly limited; however, it is generally 50 amino acids or less, preferably 30 amino acids or less, and more preferably ten amino acids or less (for example, five amino acids or less, or three amino acids or less). The amino acid modifications are preferably conservative substitutions. The present invention also includes lentiviral vectors pseudotyped with proteins comprising such modified amino acids.

The pseudotyped lentiviral vectors of the present invention can be produced by having spike proteins present at the time of virus production. For example, by expressing spike in packaging cells through transfection of a spike expression vector or through induction of expression of spike genes incorporated into the host chromosomal DNA, virus particles produced from these cells become pseudotyped with the spike proteins.

Furthermore, the present invention relates to the pseudotyped lentiviral vectors in which the RNA viruses are paramyxoviruses.

Known examples of genes encoding viral proteins of paramyxoviruses are the NP, P, M, F, HN, and L genes. The "NP, P, M, F, HN, and L genes" refers to genes encoding the nucleocapsid, phospho-, matrix, fusion, hemagglutinin-neuraminidase, and large proteins, respectively. The genes of the viruses belonging to the paramyxovirus subfamily are generally described as listed below. In general, the NP gene may also be referred to as the "N gene".

| | |
|---|---|
| Genus *Paramyxovirus* | NP P/C/V M F HN-L |
| Genus *Rubulavirus* | NP P/V M F HN (SH) L |
| Genus *Morbillivirus* | NP P/C/V M F H-L |

For example, the nucleotide sequence of each gene in Sendai virus, which belongs to the genus Paramyxovirus of the family Paramyxoviridae, has accession numbers in the database as follows: M29343, M30202, M30203, M30204, M51331, M55565, M69046, and X17218 for the NP gene; M30202, M30203, M30204, M55565, M69046, X00583, X17007, and X17008 for the P gene; D11446, K02742, M30202, M30203, M30204, M69046, U31956, X00584, and X53056 for the M gene; D00152, D11446, D17334, D17335, M30202, M30203, M30204, M69046, X00152, and X02131 for the F gene; D26475, M12397, M30202, M30203, M30204, M69046, X00586, X02808, and X56131 for the HN gene; and D00053, M30202, M30203, M30204, M69040, X00587, and X58886 for the L gene.

A lentiviral vector pseudotyped with a paramyxovirus envelope protein can be produced, for example, by preparing an inactivated paramyxovirus or a virosome containing an envelope protein of a paramyxovirus, and then fusing this with a lentivirus. Alternatively, it can be produced by expressing an expression vector for expression of the paramyxovirus envelope protein in a lentiviral packaging cell.

Furthermore, the present invention relates to the pseudotyped lentiviral vectors in which the paramyxovirus is Sendai virus.

The present invention also relates to the pseudotyped lentiviral vectors in which the minus-strand RNA viruses are orthomyxoviruses.

Orthomyxoviridae viruses include the genera Influenzavirus A, Influenzavirus B, Influenzavirus C, and Thogotovirus. An Influenzavirus A includes Influenza A virus (FLUAV), an Influenzavirus B includes Influenza B virus (FLUBV), an Influenzavirus C includes Influenza C virus (FLUCV), and a Thogotovirus includes Thogoto virus (THOV) and Dhori virus (DHOV).

Known examples of genes encoding viral proteins of orthomyxoviruses are the HA, NA, and M1 genes. The "HA, NA, and M1 genes" refers to genes encoding the hemagglutinin, neuraminidase, and matrix (membrane) proteins, respectively. The genes of viruses belonging to the family Orthomyxoviridae are generally described as listed below. In general, the HA gene may also be denoted as H, and the NA gene may be denoted as N.

| | |
|---|---|
| Genus *Influenzavirus* A | PB2, PB1, PA, HA, NP, NA, M1 + M2, NS1 + NS2 |
| Genus *Influenzavirus* B | PB2, PB1, PA, HA, NP, NA + NB, M1 + M2, NS1 + NS2 |
| Genus *Influenzavirus* C | PB2, PB1, P3 (PA), HE (HA), NP, M, NS1 + NS2 |
| Genus *Thogotovirus* | PB2, PB1, PA, GP-75 (THOV), GP-64 (DHOV), NP, M |

For example, the nucleotide sequences of envelope genes of Influenzavirus A virus belonging to the genus Influenzavirus A of Orthomyxoviridae have accession numbers in the database as follows: NC_002017 for the HA gene and NC_002018 for the NA gene.

The nucleotide sequences of envelope genes of Influenza B virus belonging to the genus Influenzavirus B have accession numbers as follows: NC_002207 for the HA gene and NC_002209 for the NA gene.

The nucleotide sequence of an envelope gene of Influenza C virus belonging to the genus Influenzavirus C has accession number NC_006310 for the HE (hemagglutinin-esterase precursor) gene in the database.

The nucleotide sequence of an envelope gene of Dhori virus belonging to the genus Thogotovirus has accession number NC_006506 for the GP-64 gene in the database.

Furthermore, the present invention relates to the pseudotyped lentiviral vectors in which the orthomyxoviruses are influenzaviruses.

The present invention also relates to the pseudotyped lentiviral vectors in which the minus-strand RNA viruses are filoviruses.

Filoviridae includes the genus Marburg-like viruses, and the genus Ebola-like viruses. The genus Marburg-like viruses includes Marburg viruses, and the genus Ebola-like viruses includes the Zaire strain, Reston strain, and Sudan strain of Ebola hemorrhagic fever virus. Any of the above-mentioned strains can be used as Ebola hemorrhagic fever virus in the present invention. Preferably the Zaire strain of Ebola hemorrhagic fever virus is used.

For example, the nucleotide sequences of genes encoding viral proteins of Ebola hemorrhagic fever in the database have accession numbers NC_002549, L11365, AF086833, AF272001, U28077, U31033, and AY142960.

Furthermore, the present invention relates to the pseudotyped lentiviral vectors in which the filovirus is Ebola hemorrhagic fever virus.

The present invention also relates to the pseudotyped lentiviral vectors in which the plus-strand RNA viruses are coronaviruses.

Coronaviridae includes the genus Coronavirus and the genus Torovirus. Examples of the genus Coronavirus include SARS virus, infectious bronchitis virus, human coronavirus, and murine hepatitis virus, and examples of the genus Torovirus include equine torovirus and human torovirus.

For example, the nucleotide sequences of genes encoding viral proteins of SARS virus in the database have accession numbers NP_828851 for a spike protein and NC_004718.

Furthermore, the present invention relates to the pseudotyped lentiviral vectors in which the coronavirus is SARS virus.

The present invention also relates to the pseudotyped lentiviral vectors in which the DNA viruses are baculoviruses. Since spike proteins of baculoviruses have structural similarities to spike proteins of influenza D virus such as Thogoto, it is suggested that baculoviruses can infect the airway epithelium (Sinn, P. L., Burnight, E. R., Hickey, M. A., Blissard, G. W., and McCray, P. B., Jr. Persistent gene expression in mouse nasal epithelia following feline immunodeficiency virus-based vector gene transfer. J. Virol. (2005) 79: 12818-12827). Baculoviruses in the present invention include, for example, *Autographa californica.*

For example, when the minus-strand RNA viruses are paramyxoviruses, the lentiviral vectors of the present invention pseudotyped with RNA virus or DNA virus spike proteins preferably comprise the HN protein and F protein. When the minus-strand RNA viruses are orthomyxoviruses, the vectors preferably comprise not only the HA protein but also the NA protein, the GP88 protein, or HE. When the RNA viruses are coronaviruses, the vectors preferably comprise the S protein. When the RNA viruses are filoviruses, the vectors preferably comprise envelope proteins.

In the present invention, it was demonstrated that pseudotyped simian immunodeficiency virus vectors containing the HN and F proteins of Sendai virus show high efficiency of gene transfer into airway epithelial stem cells. Specifically, lentiviral vectors of the present invention include pseudotyped simian immunodeficiency virus vectors containing the F and HN proteins. Furthermore, pseudotyped simian immunodeficiency virus vectors of the present invention may further contain the paramyxovirus M protein.

The simian immunodeficiency virus (SIV) was discovered as a monkey-derived HIV-like virus. Along with HIV, SIV focus the primate lentivirus group (E. Ido and M. Hayamizu, "Gene, Infection and Pathogenicity of Simian Immunodeficiency Virus", Protein, Nucleic acid and Enzyme, Vol. 39, No. 8, p. 1425, 1994). This group is further divided into four subgroups:

(1) the HIV-1 subgroup: containing HIV-1, the virus which causes human acquired immune deficiency syndrome (AIDS), and SIV cpz isolated from chimpanzees;

(2) the HIV-2 subgroup: containing SIV smm isolated from Sooty Mangabeys (*Cercocebus atys*), SIV mac isolated from rhesus monkeys (*Macaca mulatta*), and HIV-2, which is less pathogenic in humans (Jaffar, S. et al., J. Acquir. Immune Defic. Syndr. Hum. Retrovirol., 16(5), 327-32, 1997);

(3) the SIVagm subgroup: represented by SIVagm isolated from African green monkeys (*Cercopithecus aethiops*); and (4) the SIVmnd subgroup: represented by SIVmnd isolated from Mandrills (*Papio sphinx*).

SIV in the present invention includes all strains and subtypes of SIV. Examples of isolated SIV strains include SIVagm, SIVcpz, SIVmac, SIVmnd, SIVsm, SIVsnm, and SIVsyk.

There are no reports of SIVagm and SIVmnd pathogenicity in natural hosts (Ohta, Y. et al., Int. J. Cancer, 15, 41(1), 115-22, 1988; Miura, T. et al., J. Med. Primatol., 18 (3-4), 255-9, 1989; M. Hayamizu, Nippon Rinsho, 47, 1, 1989). In particular, reports of infection experiments suggest that the TYO-1 strain of the SIVagm virus is not pathogenic to cynomolgus monkeys (*Macaca facicularis*) and rhesus monkeys (*Macaca mulatta*), in addition to its natural hosts (Ali, M. et al, Gene Therapy, 1 (6), 367-84, 1994; Honjo, S et al., J. Med. Primatol., 19 (1), 9-20, 1990). There are no reports of SIVagm infection, pathogenesis or pathogenic activity in humans. In general, primate lentiviruses have strict species-specificity, and there are few reports of cross-species infection or pathogenesis from natural hosts. Where cross-species infection does occur, the frequency of disease onset is normally low, and the disease progress is slow (Novembre, F. J. et al., J. Virol., 71(5), 4086-91, 1997). Accordingly, SIV derived from the agm strain are preferably used in the present invention. Furthermore, viral vectors based on the SIVagm TYO-1 strain are thought to be safer than vectors based on HIV-1 or other lentiviruses, and are thus preferred for use in the present invention.

The pseudotyped simian immunodeficiency virus vectors of the present invention may further contain envelope proteins derived from other viruses. For example, envelope proteins derived from viruses that infect human cells are preferred as such proteins. Such proteins include, but are not particularly limited to, retroviral amphotropic envelope proteins. For example, envelope proteins derived from the murine leukemia virus (MuLV) 4070A strain can be used as retroviral amphotropic envelope proteins. Alternatively, envelope proteins derived from MuLV 10A1 can also be used (for example, pCL-10A1 (Imgenex) (Naviaux, R. K. et al., J. Virol. 70: 5701-5705 (1996)). Other examples include the envelope glycoprotein (GP) of the Zaire strain of Ebola hemorrhagic fever virus and the spike envelope protein (S protein) of severe acute respiratory syndrome (SARS) virus identified as a new type of coronavirus. Examples of proteins from the Herpesviridae include the gB, gD, gH, and gp85 proteins of herpes simplex viruses, and the gp350 and gp220 proteins of EB virus. Proteins from the Hepadnaviridae include the S protein of hepatitis B virus.

The simian immunodeficiency virus vectors of the present invention may contain a portion of a genomic RNA sequence derived from another retrovirus. Also included in the simian immunodeficiency virus vectors of the present invention are vectors comprising a chimeric sequence, resulting from replacing a portion of the simian immunodeficiency virus genome with, for example, a portion of the genomic sequence of another lentivirus such as human immunodeficiency virus (HIV), feline immunodeficiency virus (FIV) (Poeschla, E. M. et al., Nature Medicine, 4 (3), 354-7, 1998) or caprine arthritis encephalitis virus (CAEV) (Mselli-Lakhal, L. et al., Arch. Virol., 143 (4), 681-95, 1998).

In retroviruses, the LTR (long terminal repeat) may also be modified. The LTR is a retrovirus-specific sequence, which is present at both ends of the viral genome. The 5' LTR serves as a promoter, enhancing proviral mRNA transcription. Thus, it may be possible to enhance mRNA transcription of the gene transfer vector, improve packaging efficiency, and increase vector titer if the portion exhibiting the 5' LTR promoter activity in the gene transfer vector is substituted with another promoter having stronger promoter activity. Furthermore, for example, in the case of lentiviruses, the viral protein tat is known to enhance 5' LTR transcription activity, and therefore, substitution of the 5' LTR with a promoter independent of the tat protein will enable the exclusion of tat from the packaging vectors. After RNAs of viruses which have infected or invaded cells are reverse transcribed, the LTRs at both ends are linked to form a closed circular structure, viral integrase couples with the linkage site, and this structure is then integrated into cell chromosomes. The transcribed proviral mRNAs consist of the region ranging from the 5' LTR transcription initiation site to the 3' LTR polyA sequence located downstream. The 5' LTR promoter portion is not packaged in the virus. Thus, even if the promoter is replaced with another sequence, the portion integrated into target cell chromosomes is unchanged. Based on the facts described above, substitution of the 5' LTR promoter is thought to provide a safer vector with a higher titer. Thus, substitution of the promoter at the 5' end of a gene transfer vector can increase the titer of a packageable vector.

Safety can be improved in recombinant simian immunodeficiency virus vectors by preventing transcription of the full-length vector mRNA in target cells. This is achieved using a self-inactivating vector (SIN vector) prepared by partially eliminating the 3' LTR sequence. The lentivirus provirus that has invaded the target cell chromosomes, has its 5' end bound to the U3 portion of its 3' LTR. Thus, the U3 portion is located at the 5' end in the gene transfer vector, and from that point, the whole RNA of the gene transfer vector is transcribed. If there are lentiviruses or similar proteins in target cells, it is possible that the gene transfer vector may be re-packaged and infect other cells. There is also a possibility that the 3' LTR promoter may express host genes located at the 3' side of the viral genome (Rosenberg, N., Jolicoeur, P., Retroviral Pathogenesis. Retroviruses. Cold Spring Harbor Laboratory Press, 475-585, 1997). These events are already considered to be problems of retroviral vectors, and the SIN vector was developed as a way of overcoming these problems (Yu, S. F. et al., Proc. Natl. Acad. Sci. USA, 83 (10), 3194-8, 1986). When the 3' LTR U3 portion is deleted from a gene transfer vector, target cells lack the promoters of 5' LTR and 3' LTR, thereby preventing the transcription of the full-length viral RNA and host genes. Furthermore, since only the genes of interest are transcribed from endogenous promoters, highly safe vectors capable of high expression can be expected. Such vectors are preferable in the present invention. SIN vectors can be constructed according to known methods.

One problem encountered in gene therapy using viral vectors that have the LTR sequence in their genome, including retroviral vectors, is a gradual decrease in expression of an introduced gene. One factor behind this may be that when such a vector is integrated into the host genome, a host mechanism methylates the LTR to suppress expression of the introduced gene (Challita, P. M. and Kohn, D. B., Proc. Natl. Acad. Sci. USA 91: 2567, 1994). One advantage of SIN vectors is that LTR methylation hardly reduces gene expression level. This is because the vector loses most of the LTR sequence upon integration into the host genome. An SIN vector prepared by substituting another promoter sequence for the 3' LTR U3 region of a gene transfer vector, was found to maintain a stable expression for more than two months after introduction into primate ES cells (WO 02/101057). Thus, an SIN vector designed to self-inactivate by the modification of the LTR U3 region is especially suitable in the present invention.

Examples of lentiviral vectors of the present invention other than the above-mentioned simian immunodeficiency virus vectors include equine infectious anemia virus (EIAV) vectors, human immunodeficiency virus (HIV, for example HIV1 or HIV2) vectors, and feline immunodeficiency virus (FIV) vectors.

A risk that has been pointed out concerning lentivirus vectors such as HIV vectors is that if the host genome already has an HIV provirus, recombination may occurs between a foreign vector and the endogenous provirus, leading to production of replication-competent viruses. This is predicted to become a serious problem in the future, when HIV vectors are used in HIV patients. The SIV vectors used in the present invention have low sequence homology with HIV, and are replication-incompetent because 80.6% of the virus-derived sequence has been removed from the vectors. Thus, these vectors do hardly pose this risk and are safer than other lentiviral vectors. Accordingly, of these lentiviral vectors, simian immunodeficiency virus (SIV) vectors are used as particularly preferred lentiviral vectors in the present invention.

The preferred SIV vectors of the present invention are replication-incompetent viruses from which 40% or more, more preferably 50% or more, still more preferably 60% or more, even more preferably 70% or more, and most preferably 80% or more of the sequence derived from the original SIV genome has been removed.

Retroviruses can be produced by transcribing in host cells gene transfer vector DNAs which contain a packaging signal and forming virus particles in the presence of gag, pol and envelope proteins. The packaging signal sequence encoded by the gene transfer vector DNAs should preferably be sufficient in length to maintain the structure formed by the sequence. However, in order to suppress the frequency of wild-type virus formation, which occurs due to recombination of the vector DNA packaging signal and the packaging vector supplying the gag and pol proteins, it is also necessary to keep sequence overlapping between these vector sequences to a minimum. Therefore, when it comes to the construction of the gene transfer vector DNAs, it is preferable to use a sequence which is as short as possible and yet still contains the sequence essential for packaging, to ensure packaging efficiency and safety.

For example, in the case of the SIVagm-derived packaging vector, the type of virus from which the signal to be used is derived may be limited to SIV, because HIV vectors are not packaged. However, an SIV-derived gene transfer vector is also packageable when an HIV-derived packaging vector is used. Thus, the frequency of recombinant virus formation can be reduced if vector particles are formed by combining a gene transfer vector and packaging vector, where each vector is derived from a different type of lentivirus. SIV vectors thus produced are also included in vectors of this invention. In such cases, it is preferable to use combinations of primate lentiviruses (for example, HIV and SIV).

In a preferred gene transfer vector DNA, the gag protein has been modified such that it is not expressed. Viral gag protein may be detected by a living body as a foreign substance, and thus as a potential antigen. Alternatively, the protein may affect cellular functions. To prevent gag protein expression, nucleotides downstream of the gag start codon can be added or deleted, introducing modifications which will cause a frameshift. It is also preferable to delete portions of the coding region of the gag protein. The 5' portion of the coding region of the gag protein is known to be essential for virus packaging. Thus, in a gene transfer vector, it is preferable that the C-terminal side of the gag protein-coding region has been deleted. It is preferable to delete as large a portion of the gag coding region as possible, so long as the deletion does not considerably affect the packaging efficiency. It is also preferable to replace the start codon (ATG) of the gag protein with a codon other than ATG. The replacement codon can be selected appropriately so as not to greatly affect the packaging efficiency. A viral vector can be produced by introducing the constructed gene transfer vector DNA, which comprises the packaging signal, into appropriate packaging cells. The viral vector produced can be recovered from, for example, the culture supernatant of packaging cells.

There is no limitation on the type of packaging cell, as long as the cell line is generally used in viral production. When used for human gene therapy, a human- or monkey-derived cell is suitable. Human cell lines that can be used as packaging cells include, for example, 293 cells, 293T cells, 293EBNA cells, SIV480 cells, u87MG cells, HOS cells, C8166 cells, MT-4 cells, Molt-4 cells, HeLa cells, HT1080 cells, and TE671 cells. Monkey cell lines include, for example, COS1 cells, COST cells, CV-1 cells, and BMT10 cells.

The type of foreign gene to be carried by the pseudotyped lentiviral vectors of the present invention is not limited.

Such genes include nucleic acids which encode proteins, and those which do not encode proteins, for example, antisense nucleic acids and ribozymes. The genes may have a natural or an artificially designed sequence. Artificial proteins include fusion proteins with other proteins, dominant-negative proteins (including soluble receptor molecules and membrane-bound dominant negative receptors), truncated cell-adhesion molecules, and soluble cell-surface molecules.

The present inventors confirmed that pseudotyped lentiviral vectors of the present invention express foreign genes for a long period of time in airway epithelial cells including airway epithelial stem cells and airway epithelial progenitor cells. Specifically, the pseudotyped lentiviral vectors of the present invention have the ability to express foreign genes in airway epithelial cells for at least 90 days or more, and more preferably 360 days or more.

Foreign genes in the present invention may be marker genes to assess the efficiency of gene transfer, stability of expression, and so on. Marker genes include genes that encode green fluorescent protein (hereinafter also referred to as "GFP"), beta-galactosidase, and luciferase. The GFP-encoding gene is particularly preferable.

Furthermore, foreign genes in the present invention may be genes encoding an inherent or acquired dysfunctional protein. Herein, the phrase "inherent dysfunctional" refers to being innately dysfunctional due to genetic factors, and the phrase "acquired dysfunctional" refers to being dysfunctional due to environmental factors after birth.

For example, in the case of cystic fibrosis (CF), examples include genes encoding inherent or acquired dysfunctional cystic fibrosis-causing factors (proteins), and preferably genes encoding inherent or acquired dysfunctional cystic fibrosis transmembrane conductance regulator (CFTR) proteins.

Alternatively, examples of foreign genes in the present invention include genes encoding proteins having therapeutic effects on cystic fibrosis.

Or otherwise, examples of foreign genes in the present invention may be genes encoding proteins that have become dysfunctional due to a genetic disease. An example is a gene encoding the CFTR protein.

The pseudotyped lentiviral vectors of the present invention can be purified to become substantially pure. The phrase "substantially pure" means that the pseudotyped lentiviral vectors contain substantially no replicable virus other than the lentivirus. The purification can be achieved using known purification and separation methods such as filtration, centrifugation, and column purification. For example, a vector can be precipitated and concentrated by filtering a vector solution with a 0.45-μm filter, and then centrifuging it at 42500×g at 4° C. for 90 minutes. If necessary, the pseudotyped lentiviral vectors of the present invention can be prepared as compositions by appropriately combining with desired pharmaceutically acceptable carriers or vehicle. The term. "pharmaceutically acceptable carrier" refers to a material that can be administered in conjunction with the vector and does not significantly inhibit vector-mediated gene transfer. Specifically, the vector can be appropriately combined with, for example, sterilized water, physiological saline, culture medium, serum, and phosphate buffered saline (PBS). The vector can also be combined with a stabilizer, biocide, and such. Compositions containing a pseudotyped lentiviral vector of the present invention are useful as reagents or pharmaceuticals. For example, compositions of the present invention can be used as reagents for gene transfer into airway stem cells, or as pharmaceuticals for gene therapy of various diseases such as genetic diseases.

A nucleic acid carried by a pseudotyped lentiviral vector of the present invention can be introduced into airway epithelial stem cells by contacting this vector with airway epithelial cells of primates including humans. The present invention relates to methods for introducing genes into airway epithelial stem cells, which comprise the step of contacting airway epithelial cells with the vectors of the present invention. The present invention also relates to uses of lentiviral vectors pseudotyped with RNA or DNA virus spike proteins for introducing genes into airway epithelial stem cells. The airway epithelial stem cells targeted for gene introduction are not particularly limited, and for example, bone marrow-derived stem cells including mesenchymal stem cells that may differentiate into the desired simian or human airway epithelium can also be used as airway epithelial stem cells.

Monkey-derived airway epithelial stem cells which are targets of gene transfer by the pseudotyped lentiviral vectors of the present invention are not particularly limited, but examples include marmoset airway epithelial stem cells, rhesus monkey airway epithelial stem cells, and cynomolgus monkey airway epithelial stem cells.

The procedure for transferring genes into airway epithelial stem cells using a pseudotyped lentiviral vector of the present invention is carried out by a method comprising the step of contacting airway epithelial cells with the vector. For example, as described below in the Examples, the vector can be contacted with the cells by administering it to the nasal cavity using a catheter.

Pseudotyped lentiviral vectors of the present invention have the advantage of yielding extremely high gene transfer efficiency even without pretreatment such as washing the cell surface before contacting the vector.

The present invention also relates to airway epithelial stem cells introduced with lentiviral vectors of the present invention pseudotyped with RNA or DNA virus spike proteins, and cells produced by proliferation and/or differentiation of these cells.

Airway epithelial stem cells to which genes have been introduced by pseudotyped lentiviral vectors of the present invention, and cells, tissues, organs and such differentiated from these airway stem cells are useful for assaying and screening for various types of pharmaceutical agents. Through gene transfer into airway epithelial stem cells, for example, pharmaceutical agents or genes for carrying out specific differentiation of tissues or cells, and particularly preferably tissues or cells derived from primates, can be evaluated for their effects or screened for.

The present invention also encompasses airway epithelial stem cells into which pseudotyped lentiviral vectors of the present invention have been introduced, and differentiated cells and tissues that have differentiated from the airway epithelial stem cells. The differentiated cells and tissues can be identified based on marker expression and morphological characteristics specific to the tissues or cells.

Furthermore, by using the pseudotyped lentiviral vectors of the present invention, genes can be efficiently introduced into and expressed in airway epithelial stem cells for a long time. Specifically, the present invention relates to agents for transferring genes into airway epithelial stem cells, which comprise as an active ingredient a pseudotyped lentiviral vector of the present invention. For example, when using the above-mentioned gene transfer agents for airway epithelial stem cells, tissues or organs such as lungs may be used as a production tissue to provide proteins needed for disease treatment.

Furthermore, since the pseudotyped lentiviral vectors of the present invention can introduce genes into airway epithelial stem cells for long periods of time as described above, they can be applied to gene therapy of genetic respiratory diseases of primates including humans. Specifically, the present invention relates to therapeutic agents for genetic respiratory diseases which comprise a pseudotyped virus vector of the present invention as an active ingredient.

The present invention also relates to methods for preventing or treating genetic respiratory diseases, which comprise the step of administering a pseudotyped lentiviral vector of the present invention to individuals (for example, patients). The "individuals" in the preventive or therapeutic methods of the present invention are preferably, for example, primates including humans, but they may be non-human animals. In the present invention, "administering to individuals" can be carried out, for example, by contacting a pseudotyped lentiviral vector of the present invention with airway epithelial cells. As described below in the Examples, the contact can be accomplished by administering the vector to the nasal cavity using a catheter.

Furthermore, the present invention relates to uses of pseudotyped lentiviral vectors of the present invention for producing therapeutic agents for genetic respiratory diseases. The targeted genetic respiratory diseases are not particularly limited, but a preferred example is cystic fibrosis.

Cells, tissues, and organs differentiated from airway epithelial stem cells into which genes have been introduced may also be used for disease treatment. For example, for diseases that develop due to deficiency or lack of a gene, treatment that supplements the deficient gene and the lack of systemically circulating enzymes, growth factors and such may be performed by introducing the gene into a chromosome of airway stem cells and transplanting these cells into the body. Such diseases are not particularly limited. Furthermore, in organ transplantation-related gene therapy, a histocompatible antigen of a non-human animal donor may be converted into a human type. Accordingly, applications that increase the success rate of xenotransplantation can be performed.

When the airway epithelial stem cells into which a gene has been introduced using a pseudotyped lentiviral vector of this invention are monkey-derived, the airway epithelial stem cells can be transplanted into disease model monkeys to provide a system useful as a treatment model of human disease. Many disease model monkeys are known for various human diseases. For example, model monkeys for human Parkinson's disease can be produced artificially; many naturally diabetic monkeys are bred as accurate models of human diabetes; and SIV infection in monkeys is well known to serve as an accurate model of HIV infection in humans. For such diseases, a system where simian airway epithelial stem cells are transplanted into disease model monkeys as a preclinical test, prior to the clinical application of human airway epithelial stem cells, is exceedingly useful.

EXAMPLES

Herein below, the present invention will be specifically described with reference to the Examples, but it is not to be construed as being limited thereto. All references cited herein are incorporated as part of this description.

[Example 1] Construction of Sendai Virus Envelope Protein Expression Plasmids (1) Construction of Cytoplasmic Domain-Substituted HN Expression Plasmid An HN expression plasmid was constructed, where the cytoplasmic domain of the HN protein was substituted with the cytoplasmic domain of the SIV envelope protein (FIG. 1). After annealing three sets of synthetic oligonucleotides (Xho+Xma/Xma−Xho, Xma+131/135−Xma, 132+Bam/Bam−136), they were incorporated in turn into the XhoI-BamHI site of pBluescript KS+. A purified synthetic oligonucleotide-linked fragment obtained by digesting the aforementioned recombinant plasmid with XhoI and DraIII and a purified fragment comprising the 3' side of the HN protein obtained by digesting the HN protein expression plasmid pCAGGS-HN with DraIII and Bsu36I were incorporated into the XhoI-Bsu36I site of pCAGGS (Gene, vol. 108, pp. 193-200, 1991). The plasmid obtained by the above-mentioned method was used as the SIV cytoplasmic domain-substituted HN expression plasmid pCAGGS-SIVct/HN.

(2) Construction of SIV Cytoplasmic Domain-Added HN Expression Plasmid

An HN expression plasmid was constructed, where the cytoplasmic domain of SIV envelope protein was added to the HN protein (FIG. 2). A region containing the cytoplasmic domain of SIV envelope protein and a portion of the HN protein was amplified by PCR using primers FSIVhn and RhnSIV, and using as a template the above-mentioned cytoplasmic domain-substituted HN protein expression plasmid. After the amplified fragment was digested with XhoI and AccI, the fragment was incorporated into the XhoI-AccI site of the pBluescript KS+ (Stratagene) prepared in (1) above, into which the three sets of synthetic oligonucleotides had been inserted, to replace with the fragment containing the cytoplasmic domain of SIV envelope. A purified synthetic oligonucleotide-linked fragment obtained by digesting the aforementioned recombinant plasmid with XhoI and DraIII and a fragment comprising the 3' side of the HN protein obtained by digesting the HN protein expression plasmid pCAGGS-HN with DraIII and Bsu36I were incorporated into the XhoI-Bsu36I site of pCAGGS (Gene, vol. 108, pp. 193-200, 1991). The plasmid obtained by the above-mentioned method was used as the SIV cytoplasmic domain-added HN expression plasmid pCAGGS-SIVct+HN.

(3) Construction of Cytoplasmic Domain-Deleted F Protein Expression Plasmid

F protein expression plasmids were constructed, each of which contained the first 27, 14, or 4 residues from the 5' end of the cytoplasmic domain amino acids of F protein and thus lacked 15, 28, or 38 amino acid residues, respectively (FIG. 3). Each of the fragments lacking 15, 28, and 38 amino acids, respectively, was amplified by PCR using pairs of primers, XhFF and NotF1650, NotF1611 and NotF1581, and using as a template the plasmid pBluescript KS+/SmaI/F, in which the entire region for the F protein had been inserted into the SmaI site of pBluescript KS+ (Stratagene). The amplified fragments were digested with XhoI and NotI, and then each was inserted into the XhoI-NotI site of the plasmid that had been constructed from pCAGGS (Gene, vol. 108, pp. 193-200, 1991) by inserting an XhoI/NotI linker into the EcoRI site to construct plasmids (15 amino acid deletion: pCAGGS-Fct27; 28 amino acid deletion: pCAGGS-Fct14; 38 amino acid deletion: pCAGGS-Fct4). pCAGGS-Fct4 was used as an SIV vector for pseudotyping.

(4) Construction of Cytoplasmic Domain-Deleted F Protein Expression Plasmid to which the SIV Cytoplasmic Domain was Added Plasmids were constructed (FIG. 4) by adding the first 11 amino acids from 5' end of the SIV cytoplasmic domain (SIVct11) to cytoplasmic domain-deleted F protein expression plasmids (the numbers of amino acids in the cytoplasmic domain of F protein are the same as those in the plasmids prepared in (3) above). Fragments corresponding to the above-described three types lacking the amino acids but containing the SIV cytoplasmic domain added were amplified by PCR using the pairs of primers XhFF and SA-F1650, and SA-F1611 and SA-F1581, and using as a template the plasmid pBluescript KS+/SmaI/F, in which the entire region for the F protein had been inserted into the SmaI site of pBluescript KS+ (Stratagene). The amplified fragments were digested with XhoI and NotI, and then each was inserted into the XhoI-NotI site of the plasmid that had been constructed from pCAGGS (Gene, vol. 108, pp. 193-200, 1991) by inserting an XhoI/NotI linker into the EcoRI site to construct plasmids (SIVct11 addition+15 amino acid deletion: pCAGGS-Fct27/SIVct11; SIVct11 addition+28 amino acid deletion: pCAGGS-Fct14/SIVct11; and SIVct11 addition+38 amino acid deletion: pCAGGS-Fct4/SIVct11).

The nucleotide sequences of primers used in the Examples are listed below.

```
FSIVhn:
                                    (SEQ ID NO: 9)
5'-GAGACTCGAGATGTGGTCTGAGTTAAAAATCAGG-3'

RhnSIV:
                                    (SEQ ID NO: 10)
5'-AGAGGTAGACCAGTACGAGTCACGTTTGCCCCTATCACCATCCCTAA

CCCTCTGTCCATAAAC-3'

XhFF:
                                    (SEQ ID NO: 11)
5'-CCGCTCGAGCATGACAGCATATATCCAGAGA-3'

NotF1650:
                                    (SEQ ID NO: 12)
5'-ATAGTTTAGCGGCCGCTCATCTGATCTTCGGCTCTAATGT-3'

NotF1611:
                                    (SEQ ID NO: 13)
5'-ATAGTTTAGCGGCCGCTCAACGGTCATCTGGATTACCCAT-3'

NotF1581:
                                    (SEQ ID NO: 14)
5'-ATAGTTTAGCGGCCGCTCACCTTCTGAGTCTATAAAGCAC-3'

SA-F1650:
                                    (SEQ ID NO: 15)
5'-ATAGTTTAGCGGCCGCCTATGGAGATAGAGGAACATATCCCTGCCTA

ACCCTTCTGATCTTCGGCTCTAATGT-3'

SA-F1611:
                                    (SEQ ID NO: 16)
5'-ATAGTTTAGCGGCCGCCTATGGAGATAGAGGAACATATCCCTGCCTA

ACCCTACGGTCATCTGGATTACCCAT-3'

SA-F1581:
                                    (SEQ ID NO: 17)
5'-ATAGTTTAGCGGCCGCCTATGGAGATAGAGGAACATATCCCTGCCTA

ACCCTCCTTCTGAGTCTATAAAGCAC-3'.
```

As a result, while pseudotyping of SIV with naturally-occurring envelope proteins was impossible, fusion of the cytoplasmic domain (F) and modification by hemagglutinin-neuraminidase (HN) enabled efficient pseudotyping. An SeV-F/HN pseudotyped SIV vector containing the GFP gene was produced by transient transfection in 293T cells, and this was concentrated by centrifugation using techniques generally used for VSG-G pseudotyped vectors.

[Example 2] Gene Transfer into Mouse Nasal Cavity Epithelial Cells Using the F/HN Pseudotyped SIV Vector An F/HN pseudotyped SIV vector carrying eGFP was administered using a thin catheter to the mouse nasal cavity, the left nostril, without preconditioning (n=3, 4x10e8 TU per animal; 100 μl). The duration of expression of the transgenes was day 3 to day 360, and anatomical analysis of the mouse nasal cavity sections was performed according to the method of Mery et al. (Mery et al. Toxicol. Pathol. Vol. 22, p. 353-372, 1994). GFP expression was evaluated in the nasal cavity sections located 1 to 4 mm (sections corresponding to distances of 1, 2, 3, and 4 mm) from the tip of the mouse nasal bone.

Figure 6:
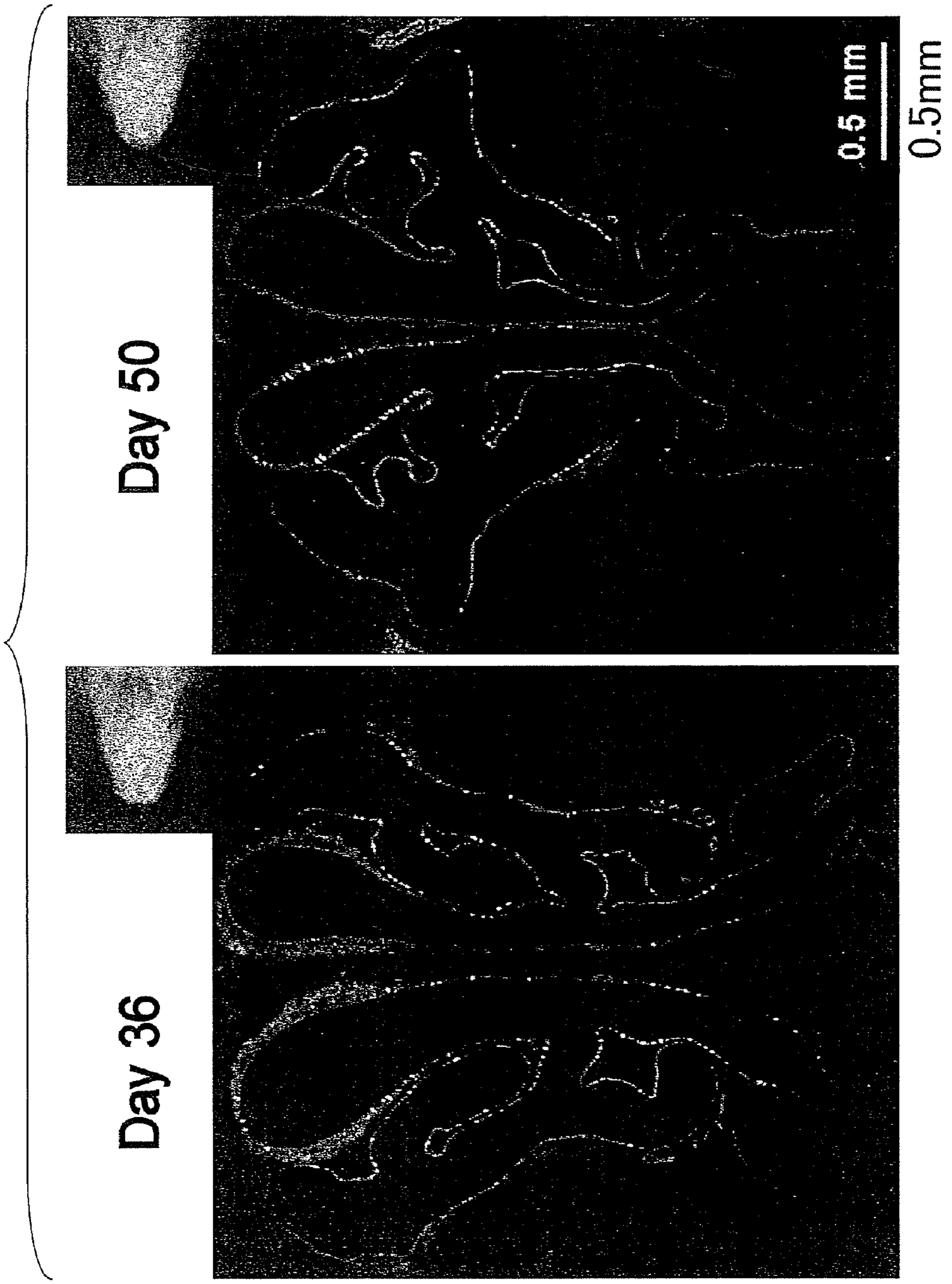
FIG. 6 shows photographs indicating that excellent specific gene transfer was observed in mouse nasal cavity epithelium due to an F/HN-pseudotyped SIV vector of the present invention. The results of day 36 and day 50 are shown. The scale bar represents 0.5 mm.
Figure 7:
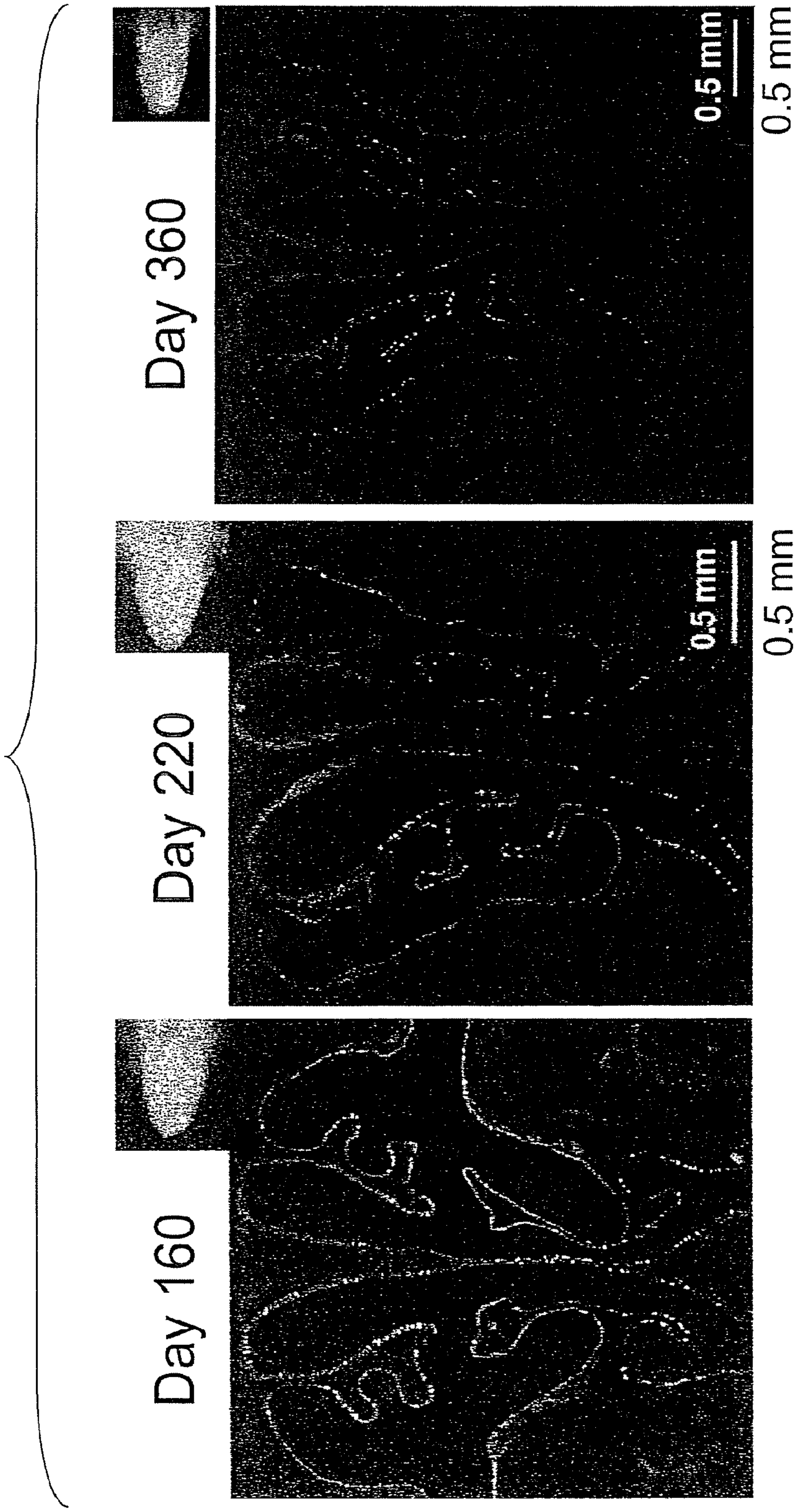
FIG. 7 is a continuation of the photographs of FIG. 6. They show that expression was observed on days 160, 220, and 360, which surpass the survival time of the cells. The scale bar represents 0.5 mm.

As a result, without preconditioning in airway epithelial cells, efficient transfection and continuous GFP expression was observed for at least 160 days. Expression of eGFP was found to be maintained even on day 220 and day 360. Since the survival time of mouse nasal cavity epithelial cells is 90 days or less (Borthwick et al. Am. J. Respir. Cell. Mol. Biol. Vol. 24, pp. 662-670, 2001), these results suggests as indirect evidence that the gene has been introduced into stem cells of the nasal cavity airway tissue (FIGS. 5 to 7).

Figure 8:
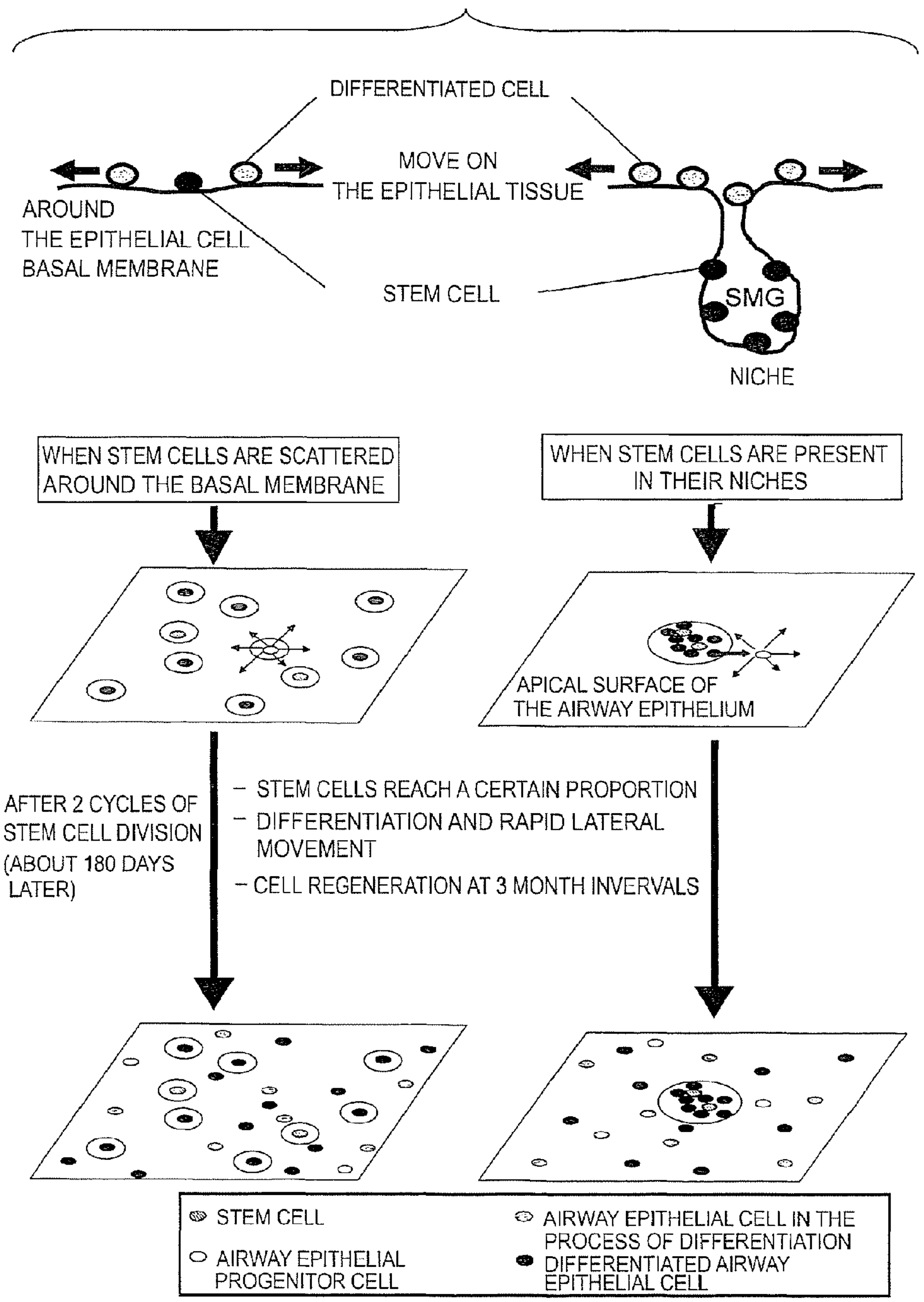
FIG. 8 is a schematic diagram that depicts the movement of differentiated cells in the epithelial tissue when stem cells are present in their niches (right) and when stem cells are scattered around the epithelial cell basement membrane (left). SMG refers to sub-mucosal gland. The four plane views at the bottom show the apical surface of the airway epithelium. The lower two plane views depict the result after two cycles of stem cell division (approximately 180 days later). When the stem cells reach a certain proportion, the differentiated cells rapidly move laterally. Cell regeneration takes place in three-month intervals. In the figure, striped (shaded) circles indicate stem cells, open circles represent airway epithelial progenitor cells, grey circles represent airway epithelial cells in the process of differentiation, and filled circles represent differentiated airway epithelial cells.

Furthermore, as shown in FIG. 8, stem cells stay in their niches when the stem cells are present in niches such as the submucosal gland (right) and when the stem cells are scattered around the epithelial cell basal membrane (left), but it is known that differentiated cells move (lateral movement) in the epithelial tissues to switch places with cells whose life has ended (J. M. W. Slack Science Vol. 287, p. 1431-1433, 2000). Therefore, GFP-positive cells were found scattered throughout the nasal cavity even on day 160, day 220, and day 360. If differentiated cells do not move, the differentiated epithelial cells should be found gathered around the stem cells. The results of the experiment suggest the possibility of the above-mentioned lateral movement.

INDUSTRIAL APPLICABILITY

The present inventors have provided for the first time recombinant simian immunodeficiency virus vectors pseudotyped with envelope glycoproteins F/HN of Sendai virus, a minus-strand RNA virus, for introducing genes into airway epithelial stem cells. By using these vectors, a gene can be introduced into airway epithelial stem cells efficiently for a long time, and the vectors are considered to be very valuable for treating genetic respiratory diseases such as cystic fibrosis. By maintaining a foreign gene in an expressible state in vectors of the present invention, where the foreign gene is, for example, a gene encoding an inherent or acquired dysfunctional protein (such as cystic fibrosis-causing factor) or a gene encoding a protein that has become dysfunctional due to a genetic disease, the vectors may become very useful for treating the above-mentioned diseases.

The invention claimed is:

1. A method of treating cystic fibrosis, the method comprising directly contacting airway epithelial tissue of an individual having cystic fibrosis with a recombinant simian immunodeficiency virus (SIV) vector comprising a cystic fibrosis transmembrane conductance regulator (CFTR) gene operably linked to a promoter, the vector pseudotyped with spike proteins of Sendai virus envelope glycoproteins F and HN, wherein the vector infects and integrates the CFTR gene into an airway epithelial stem cell genome of the airway tissue, wherein the recombinant SIV vector comprises a replication-incompetent SIV genome from which 40% to 80.6% of the original SIV genome has been removed;

wherein the airway tissue is not pretreated or pre-conditioned prior to the contacting with the vector, and wherein the integrated CFTR gene is expressed in the airway epithelial stem cell for at least 160 days thereby providing functional CFTR to treat the cystic fibrosis.

2. The method of claim 1, wherein the recombinant SIV vector is from an agm strain.

3. The method of claim 2, wherein the recombinant SIV vector is a self-inactivating (SIN) vector comprising a 3' LTR U3 region wherein the native promoter sequence of the 3' LTR U3 region is eliminated, substituted with another promoter sequence, or eliminated and substituted with another promoter sequence.

4. The method of claim 1, wherein the individual comprises a deficient CFTR gene.

5. The method of claim 4, wherein the deficient CFTR gene encodes a dysfunctional CFTR protein.

6. The method of claim 1, wherein the gene is expressed in the airway epithelial stem cell for at least 220 days or at least 360 days.

7. The method of claim 1, wherein the recombinant SIV vector is administered nasally.

8. The method of claim 1, wherein the replication-incompetent SIV genome has 60% to 80.6% of the original SIV genome removed.

* * * * *